(12) United States Patent
Gingras

(10) Patent No.: US 8,796,015 B2
(45) Date of Patent: Aug. 5, 2014

(54) TISSUE SCAFFOLD

(75) Inventor: Peter Gingras, Taylors Hill (IE)

(73) Assignee: Proxy Biomedical Limited, Galway (IE)

( * ) Notice: Subject to any disclaimer, the term of this patent is extended or adjusted under 35 U.S.C. 154(b) by 615 days.

(21) Appl. No.: 11/270,220

(22) Filed: Nov. 9, 2005

(65) Prior Publication Data

US 2006/0141012 A1    Jun. 29, 2006

(30) Foreign Application Priority Data

Nov. 9, 2004    (IE) .................................... 2004/0751

(51) Int. Cl.
    *C12N 5/00*    (2006.01)
(52) U.S. Cl.
    USPC ........... 435/325; 435/395; 424/400; 424/422; 424/426
(58) Field of Classification Search
    USPC .................. 424/400, 422, 426; 435/325, 395
    See application file for complete search history.

(56) References Cited

U.S. PATENT DOCUMENTS

| | | |
|---|---|---|
| 4,186,448 A | 2/1980 | Brekke |
| 4,661,458 A | 4/1987 | Berry et al. |
| 5,133,755 A | 7/1992 | Brekke |
| 5,282,861 A | 2/1994 | Kaplan |
| 5,514,378 A | 5/1996 | Mikos |
| 5,522,895 A | 6/1996 | Mikos |
| 5,607,474 A | 3/1997 | Athanasiou et al. |
| 5,677,355 A | 10/1997 | Shalaby et al. |
| 5,686,091 A | 11/1997 | Leong et al. |
| 5,711,960 A | 1/1998 | Shikinami |
| 5,716,413 A | 2/1998 | Walter et al. |
| 5,755,792 A | 5/1998 | Brekke |
| 5,770,193 A | 6/1998 | Vacanti et al. |
| 6,103,255 A | 8/2000 | Levene et al. |
| 6,319,264 B1 | 11/2001 | Törmälä et al. |
| 6,479,072 B1 | 11/2002 | Morgan et al. |
| 6,626,950 B2 | 9/2003 | Brown et al. |
| 2002/0142413 A1 | 10/2002 | Brady et al. |
| 2002/0182241 A1 | 12/2002 | Borenstein et al. |
| 2003/0004578 A1 | 1/2003 | Brown et al. |
| 2003/0065400 A1 | 4/2003 | Beam et al. |
| 2004/0203147 A1 | 10/2004 | Triffitt et al. |

FOREIGN PATENT DOCUMENTS

| | | |
|---|---|---|
| EP | 1277450 | 1/2003 |
| EP | 1028774 | 8/2004 |
| EP | 1452191 A2 | 9/2004 |
| EP | 1493404 | 1/2005 |
| EP | 1064958 B1 | 8/2005 |
| EP | 1131410 B1 | 10/2005 |
| WO | WO 2004/006808 | 1/2004 |
| WO | WO 2004/078954 | 9/2004 |

OTHER PUBLICATIONS

European Search Report, Application No. 05851604.8-2310 / 1816987, mailed Feb. 8, 2011 (5 pages).

*Primary Examiner* — Ruth Davis
(74) *Attorney, Agent, or Firm* — Fish & Richardson P.C.

(57) ABSTRACT

A tissue scaffold includes a first film having a plurality of cell openings and a second film adjacent the first film and having a plurality of cell openings larger than the cell openings of the first film. The cell openings of the first film interconnect with the cell openings of the second film to define pathways extending through the first and second films.

25 Claims, 49 Drawing Sheets

10

38

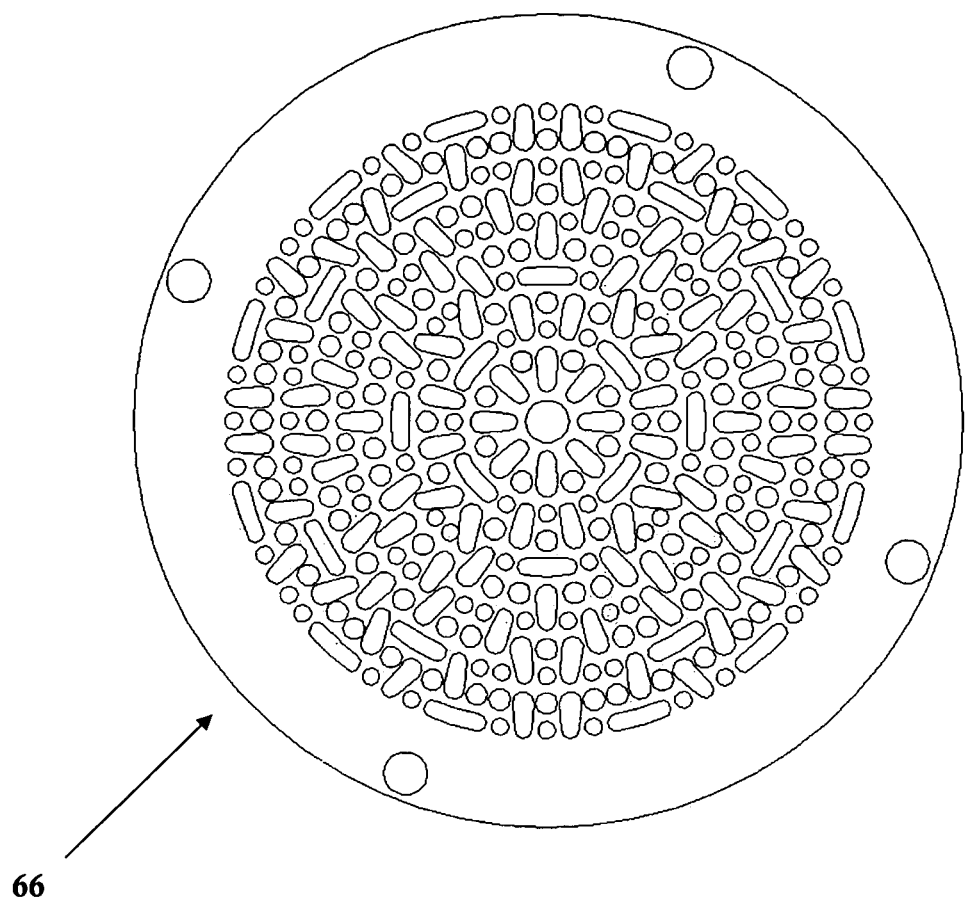
66      Fig. 3C
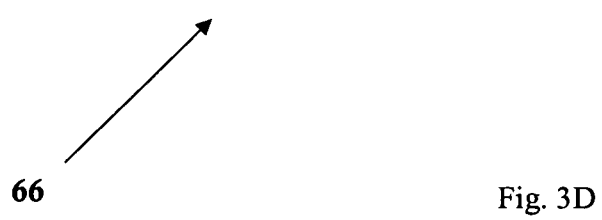
66      Fig. 3D

TISSUE SCAFFOLD

CROSS-REFERENCE TO RELATED APPLICATIONS

This application claims priority to Ireland Patent Application 2004/0751, filed on Nov. 9, 2004, the entire content of which is hereby incorporated by reference in the present application.

TECHNICAL FIELD

This application relates generally to cell and tissue scaffolds.

BACKGROUND

The field of tissue engineering has resulted in the development of biocompatible scaffolds with significant potential for use in the repair and regeneration of tissue. For example, the use of porous mesh plugs composed of hydroxy acid polymers such as polylactide for healing bone voids was described by Brekke (see U.S. Pat. No. 4,186,448). Open cell tantalum structures are described by Kaplan (see U.S. Pat. No. 5,282,861). Biodegradable and bioresorbable templates are created using leachables as described by Mikos (see U.S. Pat. Nos. 5,522,895 and 5,514,378). Multi-phase bioerodible implants and methods have been described by Athanasiou (see U.S. Pat. No. 5,607,474). Scaffolds can also be produced using vacuum foaming techniques as described by Brekke (see U.S. Pat. Nos. 5,755,792 and 5,133,755). Molded porous biodegradable polymer implants can also be created as described by Walter (see U.S. Pat. No. 5,716,413). A biodegradable foam useful for cell transplantation is described by Leong (see U.S. Pat. No. 5,686,091). A polymeric foam with continuous open cell pores containing living cells is described by Shalaby (see U.S. Pat. No. 5,677,355). The preparation of a three-dimensional fibrous scaffold for attaching cells to produce vascularized tissue in vivo is described by Vacanti (see U.S. Pat. No. 5,770,193). Textile based porous scaffolds have also been described (see U.S. Pat. Nos. 5,770,193 and 5,711,960). A hernia mesh with two or more functional components or layers with different degradation rates is described by Tormala (see U.S. Pat. No. 6,319,264). Microfabricated membranes and matrices with a three-dimensional topography are described by Morgan (see U.S. Pat. No. 6,479,072). Foam based scaffolds have also been described by Vyakarnam (see EP 1452191A2 and EP 1064958B1). Two layered structures based on cultured cells are described by Murphy (see EP 1131410B1).

SUMMARY

The present invention features tissue scaffolds and methods of making and using these scaffolds for tissue engineering. For example, the scaffolds can be configured to facilitate tissue regeneration (e.g., bone or muscle formation) or to replace tissues such as adipose tissue (as may be required in cosmetic or reconstructive surgeries), blood vessels and valves (as may be required in connection with angioplasties, vessel inflammation, or valve deterioration), or skin (as may be required where the skin is damaged by heat or mechanical force or by disease (e.g., by diabetic ulcers)). We tend to use the terms "tissue scaffold(s)" and "scaffold(s)" interchangeably. As the scaffolds are intended for use with patients, the materials from which they are made are substantially non-toxic. Accordingly, we may also refer to "biocompatible (tissue) scaffolds".

The scaffolds can include two or more films having properties that can be varied to alter the tissue scaffold's features (e.g., strength, void or "open space" volume, porosity, and durability) and performance. One or more of the films can include a plurality of cell openings, each of which defines a pore. Cell openings within the plurality can vary in size and/or shape and may be uniform or non-uniform within a given film or scaffold. For example, the tissue scaffold can have, or can include, a first film including a plurality of cell openings and a second film, adjacent the first film, that includes a plurality of cell openings that vary in size, shape, or pattern from those of the first film (e.g., the cell openings of the second film can be of the same shape or pattern but larger than the cell openings of the first film). In embodiments where the size of the cell openings vary, at least one of the first and second films can include progressively larger cell openings along a radial direction to define a cell opening gradient. Alternatively, at least one of the first and second films can include a plurality of cell openings sized and configured to define a cell opening gradient along the film. Thus, the size and/or pattern of the cell openings can be altered to generate a radial or axial porosity gradient within a film. Where size remains constant, an increase in the density of the cells openings can be used to increase porosity or to generate a porosity gradient. In any embodiment where a film includes progressively larger cell openings to define a cell opening gradient, that gradient can be defined radially or axially.

Moreover, the cell openings of the first film can interconnect with the cell openings of the second film to define pathways extending from the first film to the second film. We may refer to these pathways as interconnecting pores or regions of interconnectivity. The regions of interconnectivity can be generated or altered by orienting or altering the orientation of any one film to another (e.g., the orientation of a first film with respect to a second). The regions of interconnectivity can be substantially identical within a scaffold or may vary as the cell pattern(s) within the films vary. For example, in a first orientation of the first film with respect to the second film, the cell openings of the first film can be aligned with the cell opening of the second film to define a first plurality of pathways; in a second orientation of the first film with respect to the second film, the cell openings of the first film can be substantially offset from the cell openings of the second film to define a second plurality of pathways. In addition, the design of the cell opening pattern of the first film or a first pair or group of films can be the same as or different from the design of the cell opening pattern of the second film or a second pair or group of films. The porosity of one scaffold can be the same as that of another, even where the orientation of the films within the scaffolds is different.

The tissue scaffolds can also include a plurality of delivery channels (which we may refer to more simply as "channels") extending from the first film to the second film. Like the cell openings and the pores they define, the delivery channels can vary in size, shape, or pattern and can be uniform or non-uniform within a given film or scaffold.

At least one of the first and second films, and up to all of the films within a scaffold, can also include features to align the cell openings of the first and second films when joined together. The films can be joined thermally, mechanically (e.g., by a suture or staple) or chemically (e.g., by a biocompatible adhesive).

The films can assume essentially any shape. For example, the first and second films can be substantially identical in their dimensions (as measured, e.g., by length, width, or circumference) and can be substantially circular, oval, square, rectangular, triangular, hexagonal, or irregular in outline.

The films can be manufactured from a variety of materials, which may or may not be substantially identical and may or may not be bioabsorbable. For example, the tissue scaffolds can have, or can include, a first film comprised of a first material and a second film comprised of a second material. Where the materials are bioabsorbable, the first material can have a higher absorption rate than the second material. The materials within a film (e.g., polymers and copolymers) can also be oriented with respect to one another. For example, one can apply heat and a mechanical load to orient the polymers within a film. The oriented film is stronger, and may be exponentially stronger, than a non-oriented film.

The tissue scaffolds can further include one or more therapeutic agents (e.g., growth factors), which may be included in at least one of the cell openings, pathways, or channels within a film or plurality of films. Alternatively, or in addition, the scaffolds can further include one or more types of biological cells (e.g., stem cells, progenitor cells (e.g., osteoblasts or any other partially differentiated cell), cells of an established cell line, or mature cells such as fibroblasts), which may be included in at least one of the cell openings, pathways, or channels within a film or plurality of films. The tissue scaffolds can also include one or more antibiotics, antiviral agents, or antifungal agents, or a combination thereof, and/or one or more vitamins or minerals. Biological cells can also be included. For example, the cell openings of the first and second films can be sized and configured to define multiple cell opening gradients to establish pathways for preferential cell placement, culturing (or growth), or ingrowth (e.g., from a tissue within a patient to whom the scaffold is adminstered). While therapeutic agents are described further below, we note here that they can include a naturally or nonnaturally-occurring material that substantially modifies (by suppressing or promoting) tissue adhesion.

As noted, growth factors can be incorporated into the interconnecting pores or channels of a scaffold. Suitable growth factors include cytokines, interleukins, and other peptide growth factors such as epidermal growth factor (EGF), members of the fibroblast growth factor (FGF) family, platelet-derived growth factor (PDGF), nerve growth factor (NGF), glial growth factor (GGF), vascular endothelial growth factor (VEGF), or members of the Transforming Growth Factor (TGF) family (e.g., TGF-α or TGF-β).

The interconnecting pores, the channels, or one or more surfaces of a scaffold (e.g., a surface that comes into contact with cells, tissues, or organs upon implantation in a subject) can also contain or be coated with one or more molecules involved in cell-cell adhesion or cell-matrix adhesion (i.e., an adhesion ligand). The adhesion ligand can be an adheren or cadherin and, more specifically, can be of the ICAM (intercellular adhesion molecule) family or the N-CAM (neural cell adhesion molecule) family of proteins. We expect the incorporation of adhesion ligands as pendant functionalities into our scaffolds to facilitate integrin-dependent migration of cells, such as fibroblasts and endothelial cells, to and into the scaffolds. Growth factors located therein (some of which are exemplified above) could then induce the desired differentiation and necessary mitotic effect. The growth factor(s) could also facilitate proliferation and differentiation of stem cells or progenitor cells included in the scaffold. Depending on whether the scaffold is biodegradable or not, it can serve as either a provisional or permanent matrix for in vivo tissue regeneration. Thus, the scaffolds of the invention can include, as therapeutic agents, ligands for cell adhesion; a mechanism of relatively rapid and localized matrix dissolution (the fibrin scaffold paradigm), ideally synchronized to cellular invasion; morphogenic signals to attract and retain endogenous or exogenous progenitor cells and induce their differentiation to a tissue specific pathway. Where the scaffold is biodegradable, surgical removal should not be required (and the risks associated with such surgery are avoided).

Regardless of the precise content or configuration of the films within the scaffold, at least one of the first and second films can include one or more attachment regions configured to receive surgical fastening elements or delivery devices (e.g., pipettes, needles, syringes, and the like, through which agents such as those described herein can be delivered to the scaffold).

In one embodiment, the invention features a tissue scaffold that has, or that includes: a first film having a first porosity; a second film joined to the first film and including a second porosity less than or greater than the first porosity; and a plurality of cell openings extending through the first and second films. The first porosity and the second porosity define a porosity gradient extending from the first to the second film to selectively promote cellular regeneration along the gradient.

The invention also features methods of repairing or engineering tissue and thereby treating a subject or "patient". Accordingly, the invention encompasses the use of a tissue scaffold as described herein in the repair or engineering of tissue. While we expect the methods will be carried out with human patients, the invention is not so limited. The scaffolds can be administered to tissues of non-human animals such as mammals (e.g., dogs and cats) and birds. More specifically, one can apply a scaffold as described herein to a target tissue (e.g., muscle, connective tissue such as bone, cartilage, ligaments, and tendons, a blood vessel (including an interior surface of an artery or vein), the gastrointestinal tract, a subcutaneous space, or to the skin). The scaffold can be applied in the course of a sterile surgical procedure in the same or similar manner as presently available implants are administered to tissues. Where the tissue scaffold includes films having differing properties, one can position the scaffold so that certain film(s) contact a first target tissue and certain film(s) contact a second target tissue. One or more of the properties of the film(s) contacting the first target tissue may better promote remodeling or repair of that tissue, while one or more of the properties of the film(s) contacting the second target tissue may better promote remodeling or repair of that second tissue. One can, for example, position a plurality of delivery channels extending from a first film or plurality of films to a second film or plurality of films to a predetermined region of a tissue or tissues.

The methods can further include a step in which a subject is identified or diagnosed as having a disease or condition that would benefit from application of a tissue scaffold.

The methods can further include a step in which one introduces an agent (e.g., a therapeutic agent) to the tissue through the delivery channels. Cells can be similarly introduced, with or without a therapeutic agent. Where an agent or cells is/are introduced, one can apply a pressure differential across first and second ends of the delivery channels to generate fluid flow therethrough.

The invention also features methods of making a tissue scaffold as described herein. The methods can be carried out by forming cell openings in a first film to define a first porosity (porosity being governed by a plurality of pores defined by the openings); forming cell openings in a second film to define a second porosity greater than the first porosity; aligning the first film with respect to the second film; and attaching the first and second films such that the cell openings of the first film interconnect with the cell openings of the second film to define pathways extending from the first film to the second film. The materials within the films (e.g., the polymers and copolymers described herein) can be oriented if desired by application of a mechanical force or load to the film. Of course, our characterization of size and other properties is relative. In any embodiment, the size of one cell opening in one film may be greater than, less than, or substantially the same as the size of another cell opening in another film. The same is true of other properties such as porosity; the comparators are relative.

The cell openings can be formed by any acceptable process. For example, the cell openings can be formed using laser ablation, die punching, extrusion, injection molding, electrospinning or dip coating techniques.

One of the hurdles in achieving successful cell transplantation and tissue engineering can be the lack of adequate vacsularization. In procedures where that is a concern, the scaffolds described herein having channels sufficiently large to accommodate blood vessel ingrowth can be used. In those applications, the scaffold can also include one or more therapeutic agents that promote blood vessel growth (e.g., VEGF).

The scaffolds and implants presently in use may be deficient in one or more ways and, while the present invention is not so limited, the scaffolds described herein may have one or more advantages over those previously described. For example, the present scaffolds can be constructed in a way that produces pores and channels with controlled dimensions and the properties of the films that constitute the scaffolds can be varied to predictably alter the scaffolds' characteristics in ways that favorably impact healing and cellular responses. The present scaffolds can also be configured to improve the delivery of nutrients, fluids, cells (whether autologous or xenogeneic), therapeutic agents and the like. The architecture of the present scaffolds may also be more readily controlled (e.g., from batch to batch). The porosity of current scaffolds may be approximated, and the mechanical stress/strain profiles can be too high or too low.

The details of one or more embodiments are set forth in the accompanying drawings and the description below. Other features and advantages of will be apparent from the description and drawings, and from the claims.

BRIEF DESCRIPTION OF THE DRAWINGS

FIG. 3C is a plan view of a film used to make tissue scaffolds with 300 to 1300 micron round and oval cell opening patterns.

FIG. 3D is a side view of the film of FIG. 3C used to make tissue scaffolds with 300 to 1300 micron round and oval cell opening patterns.

FIG. 6H is a perspective view of two separate tissue scaffolds with separate delivery channel openings within each scaffold in partial section to depict delivering agents or cells to the channel openings.

DETAILED DESCRIPTION

Figure 1A:
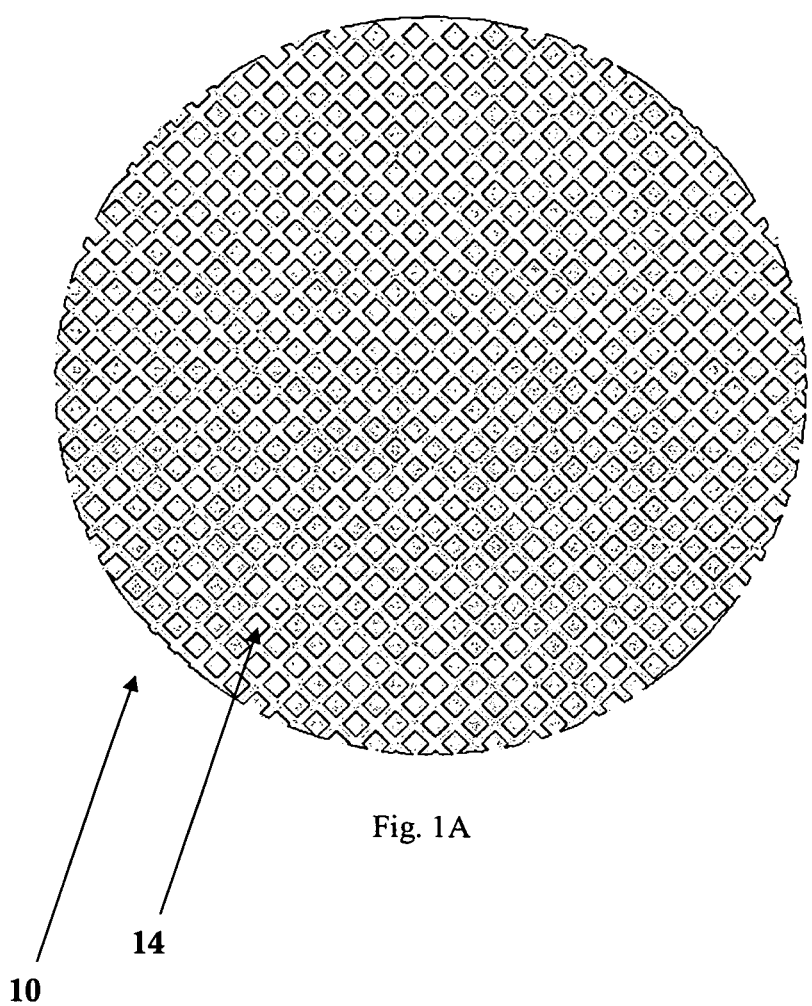
FIG. 1A is a plan view of a film used to make tissue scaffolds with 500 micron cell opening patterns.

We have generated tissue scaffolds that, in some embodiments, are biocompatible (bioresorbable or nonabsorbable) scaffolds of layered films, at least some of which are porous (macroporous or microporous) and that can provide controlled morphological and material-based gradients. The films used in the scaffolds can have a structure that provides organization at the microstructure level that facilitates cellular invasion, proliferation, and differentiation that can ultimately result in regeneration of wholly or partially functional tissue. The films of the tissue scaffold have a gradient in composition and microstructure that permits tissue ingrowth, tissue repair, tissue regeneration, and cell based research for therapeutic agent discovery. In particular the scaffold provides layered films that have been machined with openings that interface with living cells to control growth in a predictable manner.

The features of such scaffolds can be controlled to suit a desired application by choosing the appropriate conditions to form a layered film structure with openings in select areas of each film. These scaffolds have distinct advantages over the prior art where the scaffolds are isotropic or random structures.

The tissue scaffolds described herein can include cell openings (e.g., cell openings defining pores in one or more films) that vary in size and shape. Whether of a regular or irregular shape, the diameter of the cell opening can be between about 1 to about 10,000 microns. For example, cell openings can be from about 5 microns to 9,5000 microns; from about 10 to 10,000 microns; from about 25 to about 7,500 microns; from about 50 to 5,000 microns; from about 100 to about 2,500 microns; from about 100 to about 5,000 microns; from about 250 to about 2,500 microns; from about 250 to about 1,000 microns; from about 500 to about 1,000 microns; from about 750 to about 1,000 microns; or ranges therebetween. The cellular openings can provide pathways for cellular ingrowth and nutrient diffusion. Porosities can be controlled and can range from about 10% to 95% porous. Because the cell openings and/or channels can have diameters in the range of microns, useful films and scaffolds can be described as microporous. They can also be non-porous.

The features of the tissue scaffolds can be controlled to suit desired applications by selecting features to obtain the following properties: gradient along three axes for preferential cell culturing; channels that run through the scaffold for enhanced cell invasion, vascularization, and nutrient diffusion; micro-patterning of films on the surface for improved cellular organization; tailorability of pore size and shape; anisotropic mechanical properties; composite layered structure with a polymer composition gradient to modify the cellular response to different materials; blends of different polymer compositions to create structures that have portions that will degrade or resorb at different rates; films blended or coated with bioactive agents (or "compounds") included but not limited to biological factors, growth factors, and the like; ability to make three dimensional structures with controlled microstructures; and assembly with other medical devices or agents to provide a composite structure.

In some embodiments, a biocompatible scaffold includes a substantially controllable pore structure. Characteristics selected from the group comprising composition, stiffness, pore architecture, and bioabsorption rate can be controlled. The scaffold can be made from an absorbable or nonabsorbable polymers. A blend of polymers can be applied to form a compositional gradient from one layer to the next. In applications where one composition is sufficient, the scaffold provides a biocompatible scaffold that may have structural variations across one or more layers that may mimic the anatomical features of the tissue. The structural variations can result in a variation in degradation across the scaffold.

In some embodiments, the biocompatible scaffold include interconnecting pores and channels to facilitate the transport of nutrients and/or invasion of cells into the scaffold. Some channels may be created to facilitate delivery of agents, compounds or cells into the scaffold using delivery means. Positive or negative pressure methods can be employed to delivery the agents, compounds, or cells.

In one aspect, a method for the repair or regeneration of tissue includes contacting a first tissue with a scaffold pore gradient at a location on the scaffold that has appropriate characteristics to permit growth of the tissue. The concept of controlled transition in physical and chemical properties, and/or microstructural features in the scaffold can facilitate the growth or regeneration of tissue.

The scaffolds are particularly useful for the generation of tissue junctions between two or more layers of tissue. For a multi-cellular system, one type of cell can be present in one area of the scaffold and a second type of cell can be present in a separate area of the scaffold. Delivery channels can be utilized to position agents, compounds or cells in certain regions of the scaffold. Channels can also be used to generate controlled flow of a medium using positive or negative pressure means. An external source can be used to generate flow through the channels.

A gradient of absorbable polymers of different layers forming a compositional gradient from one polymeric material to a second polymeric material can be created. In situations where one composition is sufficient for the application, the scaffold provides a biocompatible film scaffold that may have microstructural variations in the structure across one or more dimensions that may mimic the anatomical features of the tissue. The cross sectional area of the implant can vary in this instance. When the scaffold degrades by surface erosion or through bulk degradation, the regions with an increased cross sectional area would degrade at a slower rate.

The films can be layered and bonded together. The films can be attached using ionic or covalent bonds. Photo-initiated bonds can be created using suitable materials such as benzaphenone. Biocompatible adhesives can be used. Alternatively, heat and pressure can be used.

The tissue scaffolds may be comprised of closed cell and open cell combinations. In this instance either the closed cell or open cell features may contain therapeutic agents or compounds. In addition, the device may comprise a stimulator that enhances the regeneration of tissue.

The materials used to produce the tissue scaffolds may be suitable for promoting the growth of either adhering, non-adhering cell lines, or any combination thereof.

In one case the material used to produce the scaffold comprises a sheet. The sheet may be substantially planar. The material may be at least partially of a layered construction. In one case the material comprises a first layer and a second layer, the first layer having a higher absorption rate than the second layer. The first layer may be located adjacent to the second layer. The second layer may be configured to be located closer to a tissue structure than the first layer.

In one embodiment the material is at least partially porous to promote tissue in-growth. The first layer may have a higher pore density than the second layer. The first layer may have a smaller pore size than the second layer. In one case at least some of the pores form at least a partial gradient with varying density.

In another embodiment the material is at least partially porous to promote tissue in-growth. The layers may have a higher pore density in select regions. The central region may have a higher pore density than the outer region. In one case at least some of the pores form at least a partial gradient from one region to the next.

The material may comprise an anti-adhesion filler filling at least some of the pores. The material may comprise an anti-adhesion coating along at least part of the surface of the material. Alternatively, a material used to promote tissue attachment and bonding may be utilised with the scaffold.

The scaffold can be produced by processing a biocompatible polymer into a film and creating a controlled pore geometry in the film (i.e., the cell openings). In alternative embodiments, the film can be stretched, oriented, or otherwise manipulated (e.g., trimmed, shaped, washed or otherwise treated) before or after forming pores in the film. Where the scaffold contains more than one film, methods can be carried out by extruding a first biocompatible polymer to form a first film, extruding a second biocompatible polymer to form a second film, attaching the first film to the second film to produce a implant, and forming pores in the implant. Alternatively, the pores can be formed before the two films are adhered to one another. In that instance, the method of making the implant can be carried out by: extruding a first biocompatible polymer to form a first film; forming pores in the first film; extruding a second biocompatible polymer to form a second film; forming pores in the second film; and attaching the first film to the second film to produce a tissue scaffold. The process can be repeated or amplified as need to produce a scaffold having the desired number of films.

As noted, the pores can have different dimensions, the films can have different thicknesses, and the films can have different compositions all of which vary the healing and biodegradation characteristics. In that instance, the method of making the scaffold can be carried out by: extruding a first biocompatible polymer to form a first film; forming pores in the first film; extruding a second biocompatible polymer to form a second film; forming pores in the second film; and attaching the first film to the second film to produce a tissue scaffold. The tissue scaffold can be designed with controlled tissue ingrowth and remodelling to permanently alter the mechanical properties of the tissue.

Where a film is obtained, rather than made, the methods of making the tissue scaffold can simply require providing a given film that is then attached (e.g., reversibly or irreversibly bound by mechanical or chemical forces), if desired, to another film and/or processed to include one or more pores of a given size and arrangement. The single provided film (or adherent multiple films) can then be subjected to a process (e.g., laser ablation, die punching, or the like) that forms pores within the film(s). Accordingly, any of the methods can be carried out by providing a given biocompatible film, rather than by producing it by an extrusion or extrusion-like process. The films used in the scaffold layers can also be produced using casting, injection moulding, electrospinning, or dip coating techniques.

Preferably, the tissue scaffolds can include a film that has ideal mechanical properties and a controlled thickness and that is biocompatible. A biocompatible film is one that can, for example, reside next to biological tissue without harming the tissue to any appreciable extent. As noted above, the film(s) used in the scaffolds can include pores (e.g., open passages from one surface of the film to another) that permit tissue ingrowth and/or cellular infiltration.

The scaffolds can offer a combination of controlled porosity, high strength, and specific material content, and they may have one or more of the following advantages. They can include pores or porous structures that stimulate tissue integration and reduce inflammation; they can reduce the risk of rejection with adjacent tissue (this is especially true with scaffolds having a smooth surface and atraumatic (e.g., smooth, tapered, or rounded edges); they can simulate the physical properties of the tissue being repaired or replaced, which is expected to promote more complete healing and minimise patient discomfort; their surface areas can be reduced relative to prior art devices (having a reduced amount of material may decrease the likelihood of an immune or inflammatory response). Moreover, scaffolds with a reduced profile can be produced and implanted in a minimally invasive fashion; as they are pliable, they can be placed or implanted through smaller surgical incisions. Methods may also produce scaffolds with improved optical properties (e.g., scaffolds through which the surgeon can visualise more of the underlying tissue). Practically, the micromachining techniques that can be used to produce the scaffolds are efficient and reproducible. The scaffolds described herein should provide enhanced biocompatibility in a low profile configuration while maintaining the requisite strength for the intended purpose.

In one embodiment, the film is made of, or includes, a biocompatible material that is biodegradable (i.e., it degrades within a human patient within a discernable period of time (e.g., within months or years)). The biocompatible material may be at least partially absorbable by the body. The biocompatible material may comprise an absorbable polymer or copolymer such as polyglycolic acid (PGA), polylactic acid (PLA), polycaprolactone, polyhydroxyalkanoate, or polyfumarate and derivatives of the above polymers.

In another embodiment, the biocompatible material is non-absorbable and can be, or can include, polypropylene, polyethylene terephthalate, polytetrafluoroethylene, polyaryletherketone, nylon, fluorinated ethylene propylene, polybutester, or silicone. The tissue scaffolds can also include a biological material such as collagen, fibrin, or elastin. Biological materials such as these can be incorporated into one or more of the films assembled into the scaffold (e.g., as a component of the film or a coating thereon) or can be contained within one or more of the pores, pathways, or channels within the scaffold.

Biocompatible materials useful in the film layers can include non-absorbable polymers such as polypropylene, polyethylene, polyethylene terephthalate, polytetrafluoroethylene, polyaryletherketone, nylon, fluorinated ethylene propylene, polybutester, and silicone, or copolymers thereof (e.g., a copolymer of polypropylene and polyethylene); absorbable polymers such as polyglycolic acid (PGA), polylactic acid (PLA), polycaprolactone, and polyhydroxyalkanoate, or copolymers thereof (e.g., a copolymer of PGA and PLA); or tissue based materials (e.g., collagen or other biological material or tissue obtained from the patient who is to receive the scaffold or obtained from another person.) The polymers can be of the D-isoform, the L-isoform, or a mixture of both. An example of a biocompatible film suitable for producing the laminated film structure is expanded polytetrafluoroethylene.

In the case of a tissue scaffold made from film layers, the various layers may be of the same or different materials. For example, in the case of an absorbable material, the material of the layers may be selected to have varying rates of absorption.

The tissue scaffolds can also include one or more materials that prevent adhesions, such as hyaluronic acid. The adhesion prevention material can coat a surface of a film, reside within one or more of the pores, pathways, or channels, or both. The adhesion prevention material may degrade as surrounding tissue heals and minimize the risk of future adhesions.

In one embodiment the biocompatible material has a plurality of cells. The biocompatible material may have a plurality of cells and one or more of the cells in the plurality of cells have a diameter, measured along the longest axis of the cell, of about 10 to about 10,000 microns. The biocompatible material may have a plurality of cells and one or more of the cells of the plurality are essentially square, rectangular, round, oval, sinusoidal, or diamond-shaped.

In one embodiment the thickness of one or more of the films within the scaffold is about or less than about 0.25 inches. For example, the scaffold can be formed from two or more films, which can be of the same or different thicknesses. For example, the films can be about or less than about 0.20 inches; about or less than about 0.18 inches; about or less than about 0.16 inches; about or less than about 0.14 inches; about or less than about 0.12 inches; about or less than about 0.10 inches; about or less than about 0.05 inches; about or less than about 0.025 inches; about or less than about 0.020 inches; about or less than about 0.015 inches; about or less than about 0.014 inches; about or less than about 0.013 inches; about or less than about 0.012 inches; about or less than about 0.011 inches; about or less than about 0.010 inches; about or less than about 0.009 inches; about or less than about 0.008 inches; about or less than about 0.007 inches; about or less than about 0.006 inches; about or less than about 0.005 inches; about or less than about 0.004 inches; about or less than about 0.003 inches; about or less than about 0.002 inches; or about 0.001 inch. In some instances, for example, where a film is non-porous, it may be thicker (e.g., about 0.5-1.0 inch thick). As noted, a given scaffold can include more than one film and the overall thickness of the scaffold can vary tremendously, depending on its intended application. For example, where the scaffold is implanted to fill a void in bone or to repair a biopsy, it can be more than an inch thick.

The tissue scaffold may comprise attachment regions, which may be adapted to receive sutures, staples or the like. In addition, the individual layers for the tissue scaffold may have alignment regions to ensure the pores in the films match up properly.

In another aspect, a method for producing a tissue scaffold, the method comprising: extruding a first biocompatible polymer to form a first film; forming cell patterns in the first film; extruding a second biocompatible polymer to form a second film; forming cell patterns in the second film; attaching the first film to the second film to produce a tissue scaffold; wherein the method may further comprise the optional step of cleaning the scaffold.

In the case of a layered scaffold, the various layers may be of the same or different materials. For example, in the case of an absorbable material, the material of the layers may be selected to have varying rates of absorption.

Medical applications for the tissue scaffolds described above may include but are not limited to tissue repair of bone, spine disc, articular cartilage, meniscus, fibrocartilage, tendons, ligaments, dura, skin, vascular grafts, nerves, liver, and pancreas. The tissue scaffold may be produced in a variety of shapes and sizes for the particular indication. One may select a non-absorbable scaffold for tissue defects that require permanent treatment and long-term durability and strength. Alternatively, one may select an absorbable scaffold for tissue defects that require temporary treatment when one wants to avoid the potential complications associated with a permanent implant.

In addition, the tissue scaffolds can be produced in three-dimensional forms to facilitate sizing. An example is a scaffold with a curvature to construct a substantially cylindrical shape. A three dimensional structure could be machined using a system incorporating a third axis for micromachining. Alternatively, a substantially two-dimensional tissue scaffold could be thermoformed into a three-dimensional shape after machining.

Figure 1B:
FIG. 1B is a side view of the film of FIG. 1A used to make tissue scaffolds with 500 micron cell opening patterns.
Figure 1C:
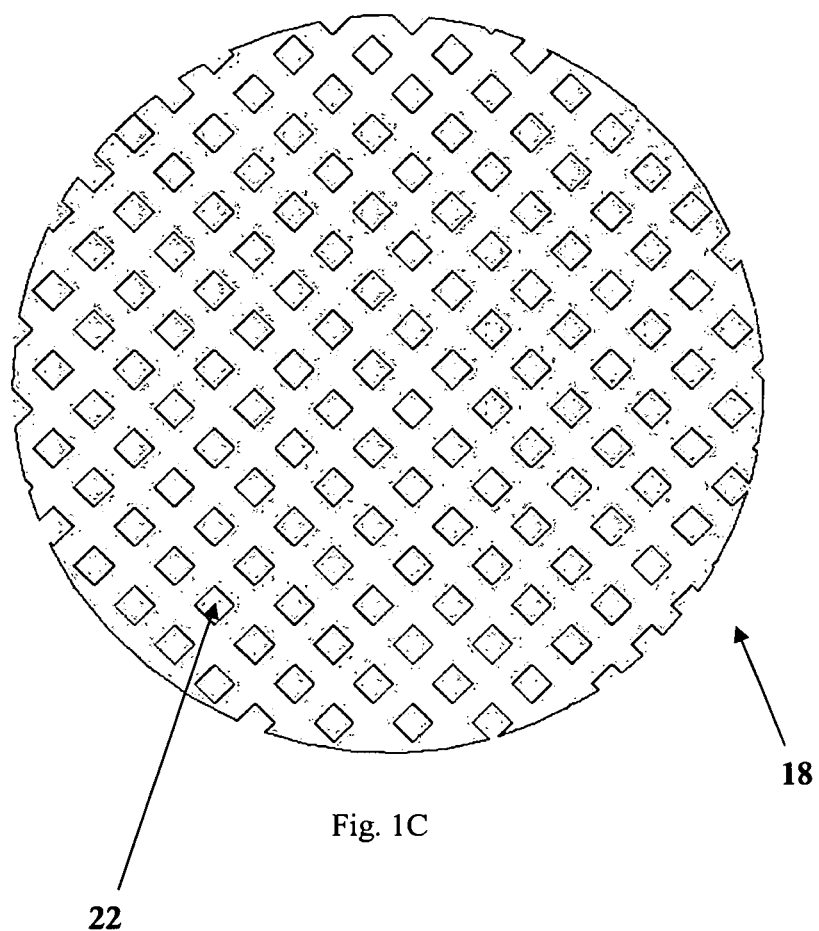
FIG. 1C is a plan view of a film used to make tissue scaffolds with 750 micron cell opening patterns.
Figure 1D:
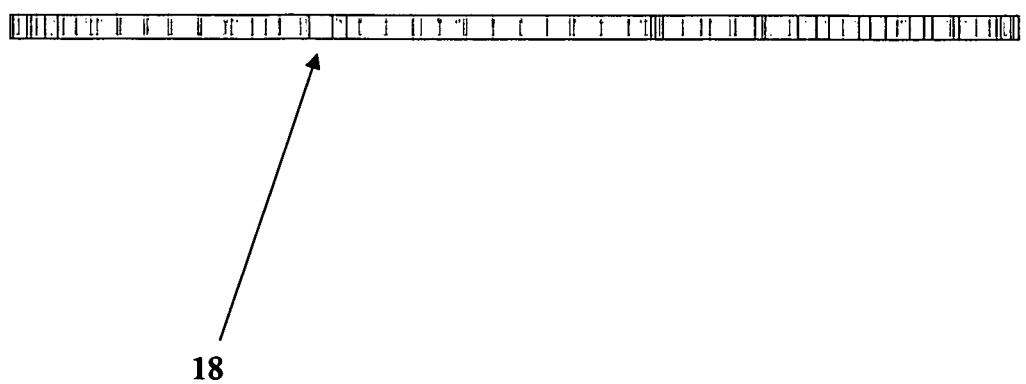
FIG. 1D is a side view of the film of FIG. 1C used to make tissue scaffolds with 750 micron cell opening patterns.
Figure 1E:
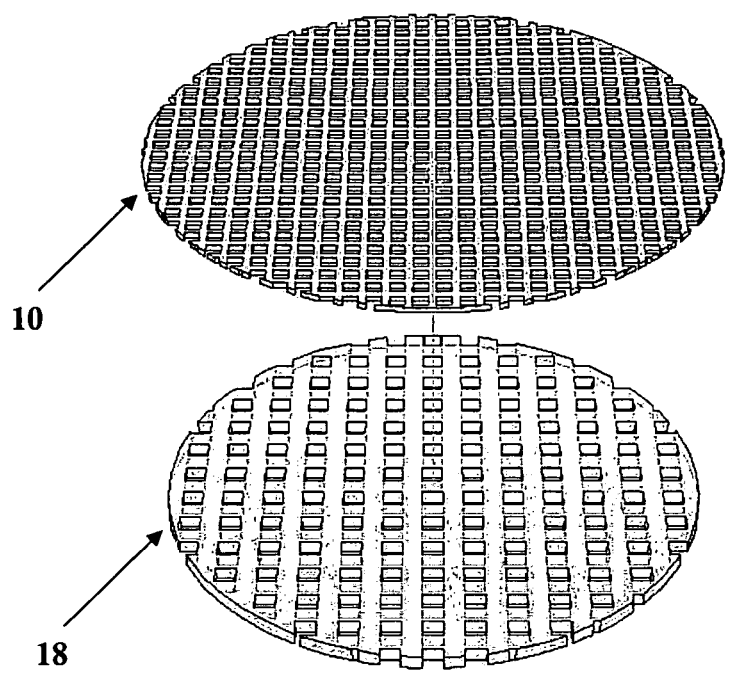
FIG. 1E is a perspective view of two films used to make tissue scaffolds with different offset cell opening patterns.
Figure 1F:
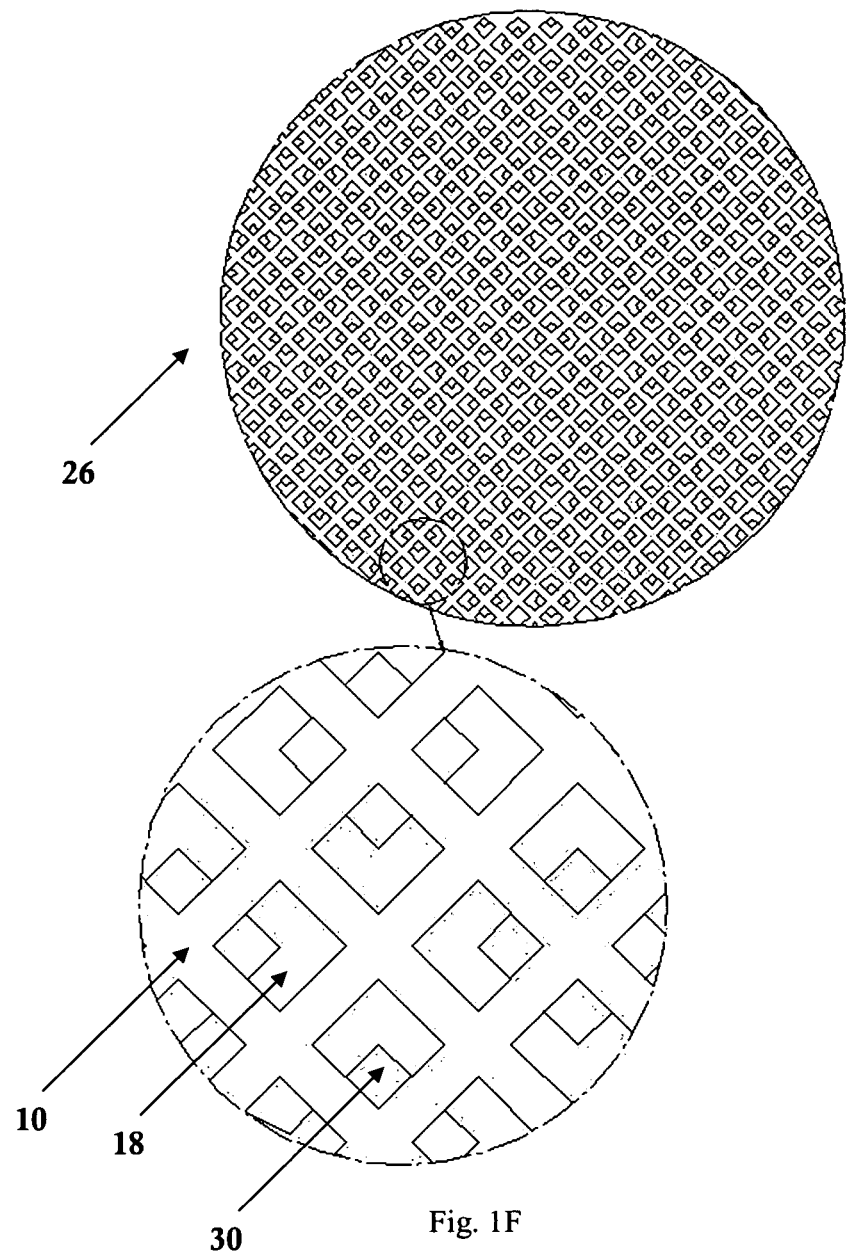
FIG. 1F is a plan view of two films used to make tissue scaffolds with different cell opening patterns offset combined to create a 250 micron interconnecting pore.
Figure 1G:
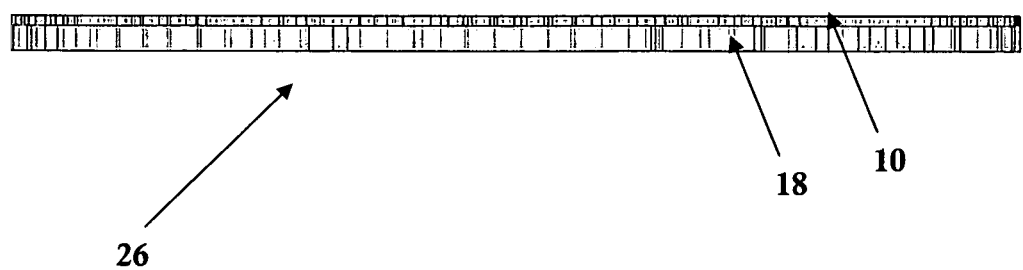
FIG. 1G is a side view of the two films of FIG. 1F used to make tissue scaffolds with different cell opening patterns combined to create a 250 micron interconnecting pore.
Figure 1H:
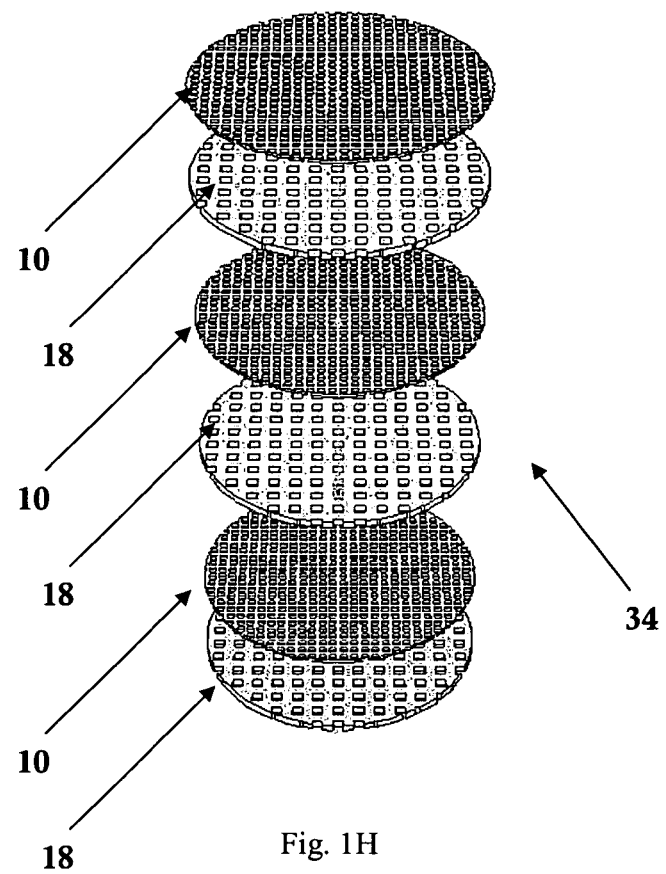
FIG. 1H is a perspective view of six films used to make tissue scaffolds with different cell opening patterns.
Figure 1I:
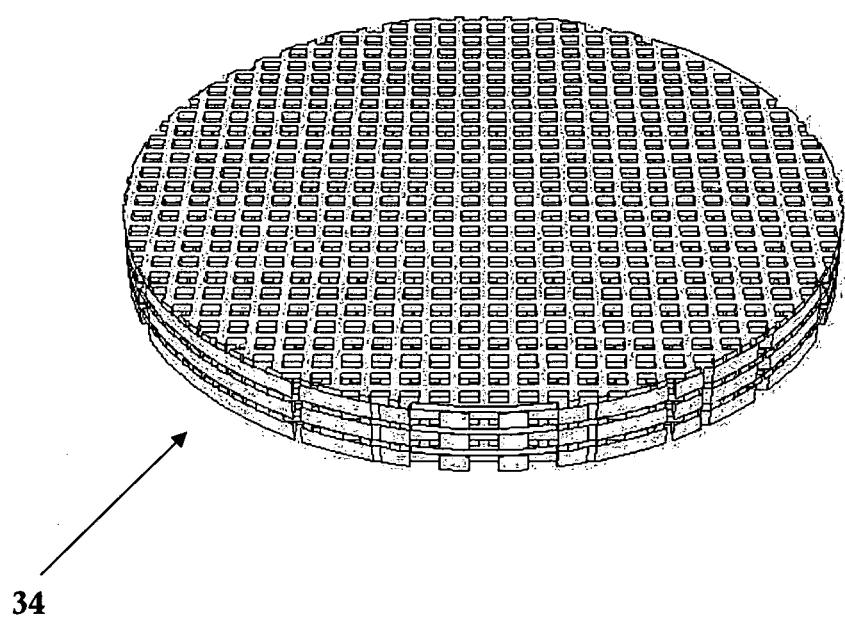
FIG. 1I is a perspective view of six films used to make tissue scaffolds with different cell opening patterns combined to create a 250 micron interconnecting pore.
Figure 1J:
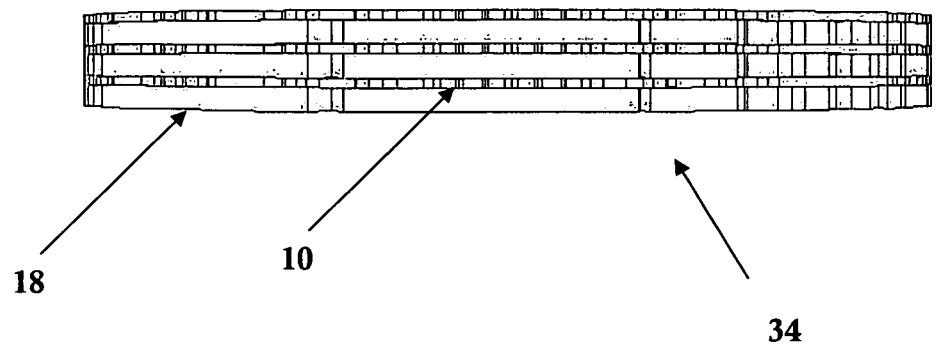
FIG. 1J is a side view of the six films of FIG. 1I used to make tissue scaffolds with different cell opening patterns combined to create a 250 micron interconnecting pore.
Figure 1K:
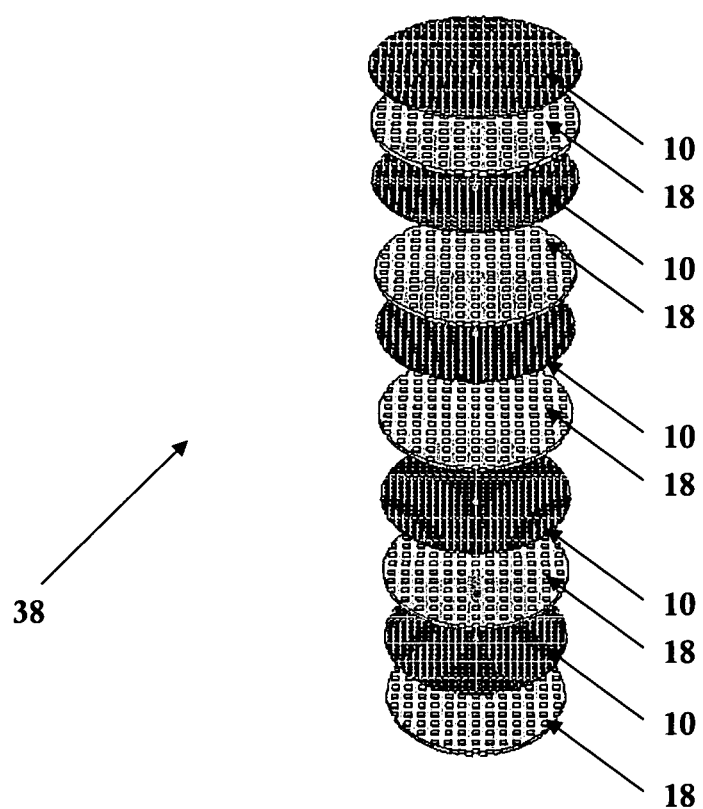
FIG. 1K is a perspective view of ten films used to make tissue scaffolds with different cell opening patterns.
Figure 1L:
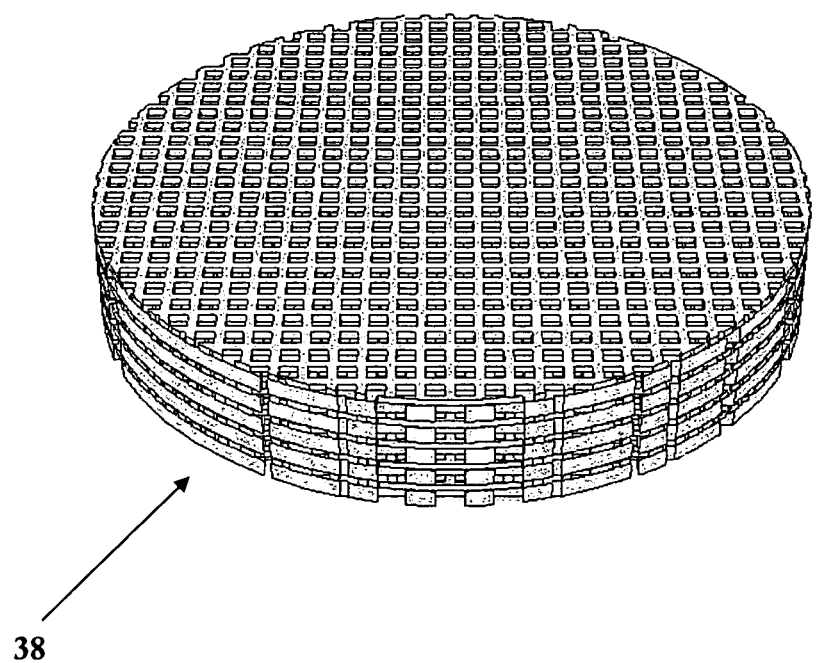
FIG. 1L is a perspective view of the ten films of FIG. 1K used to make tissue scaffolds with different cell opening patterns combined to create a 250 micron interconnecting pore.
Figure 1M:
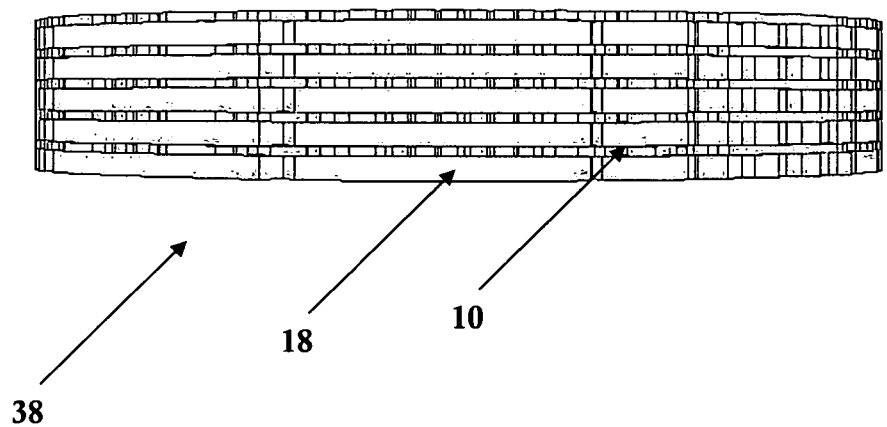
FIG. 1M is a side view of six films used to make tissue scaffolds with different cell opening patterns combined to create a 250 micron interconnecting pore.
Figure 1N:
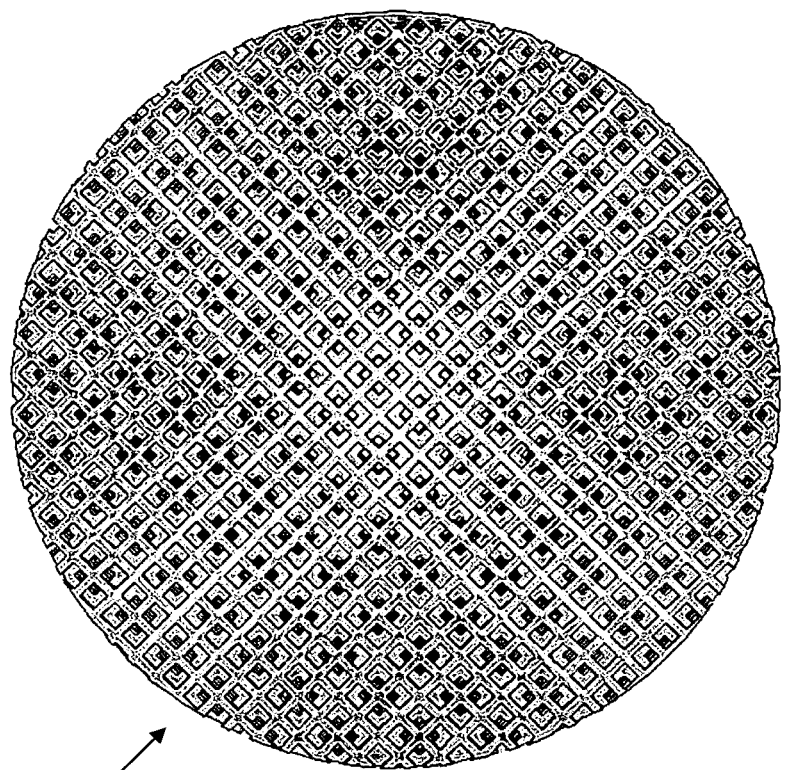
FIG. 1N is a plan view of ten films used to make tissue scaffolds with different cell opening patterns combined to create a 250 micron interconnecting pore.
Figure 1O:
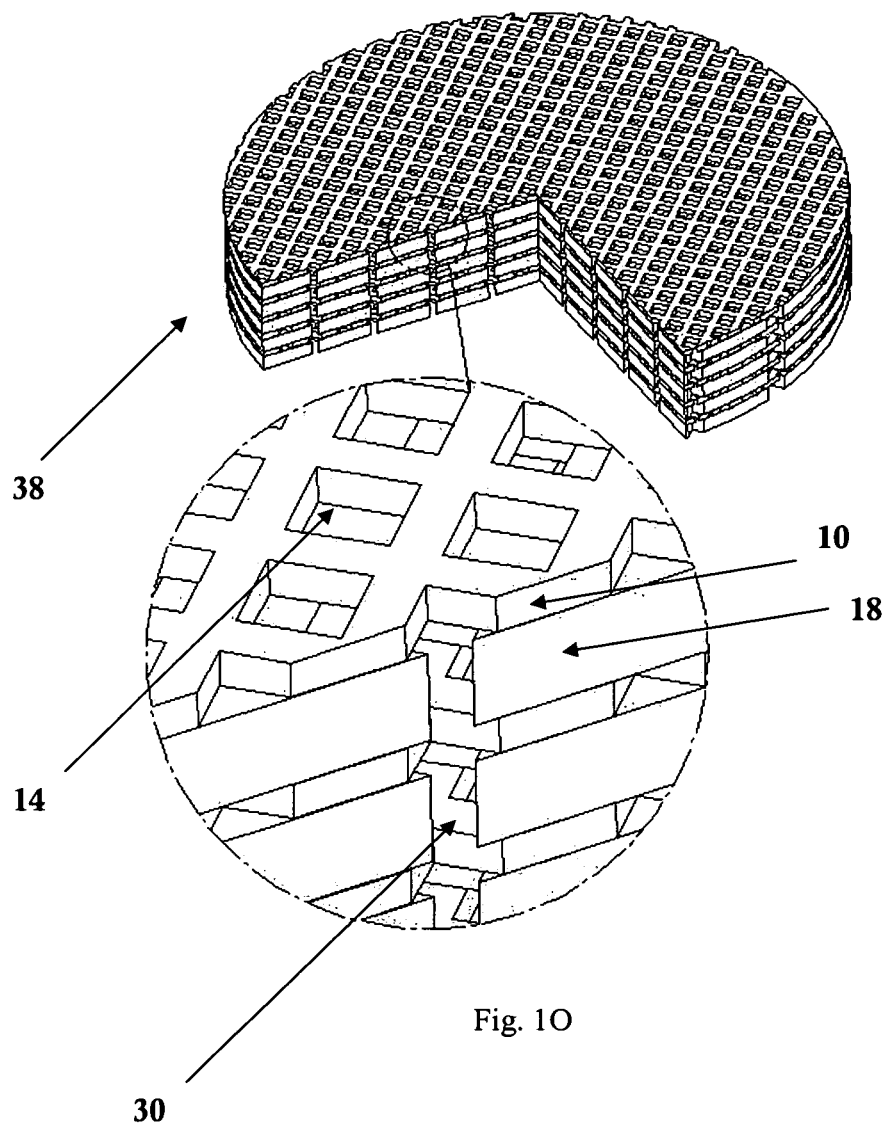
FIG. 1O is a perspective view of ten films used to make tissue scaffolds with different cell opening patterns combined to create a 250 micron interconnecting pore in partial section.

Referring collectively to FIGS. 1A-1O, film layers including cell openings of predetermined size and configuration can be combined to form a tissue scaffold. FIG. 1A illustrates a film layer 10 used to make a tissue scaffold with diamond shaped 500 micron cell openings 14 in a predetermined arrangement. The film layer 10 has known or discernable dimensions (width, length, and thickness), which can be modified or left intact during the manufacture of a tissue scaffold. Film layer 10 is a single layer. FIG. 1B is a side view of a film layer 10 used to make a tissue scaffold. FIG. 1C is a perspective view of a film layer 18 used to make a tissue scaffold with diamond shaped 750 micron cell openings 22 in a predetermined arrangement. The film layer 18 has known or discernable dimensions (width, length, and thickness), which can be modified or left intact during the manufacture of a tissue scaffold. Film layer 18 is a single layer. FIG. 1D is a side view of a film layer 18 used to make a tissue scaffold. FIG. 1E is a perspective view of film layer 10 and film layer 18 used to make a tissue scaffold with different offset cell opening patterns. As shown in FIG. 1F, film layer 10 and film layer 18 can be combined to form a two film layer tissue scaffold 26. The cell openings from the first film layer 10 are offset and interconnect with the cell openings from the second film layer 18 to create a 250 micron interconnecting pore 30. FIG. 1G is a side view of film layer 10 and film layer 18 forming a two layer tissue scaffold 26. FIGS. 1H-J are perspective views of six film layers used to make a six layer tissue scaffold 34. FIGS. 1K-O are perspective views of ten film layers used to make a ten layer tissue scaffold 38. FIG. 1O illustrates the combination of film layers 10 and film layers 18 to create an interconnecting pore 30.

Figure 2A:
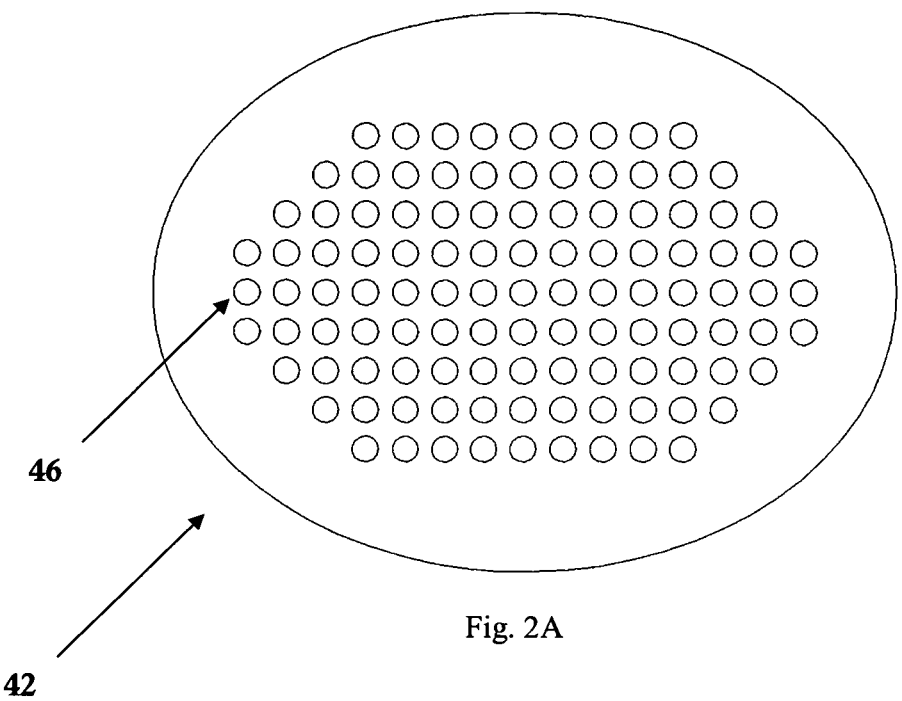
FIG. 2A is a plan view of a film used to make tissue scaffolds with 1000 micron round cell opening patterns.
Figure 2B:
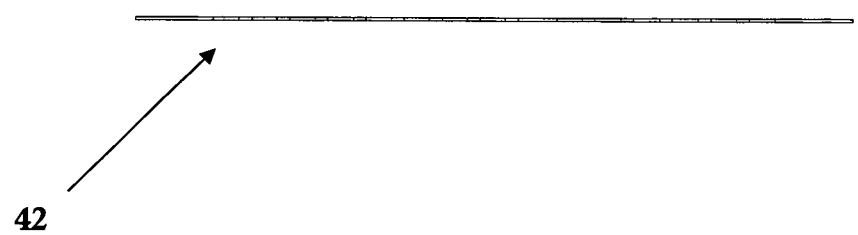
FIG. 2B is a side view of the film of FIG. 2A used to make tissue scaffolds with 1000 micron round cell opening patterns.
Figure 2C:
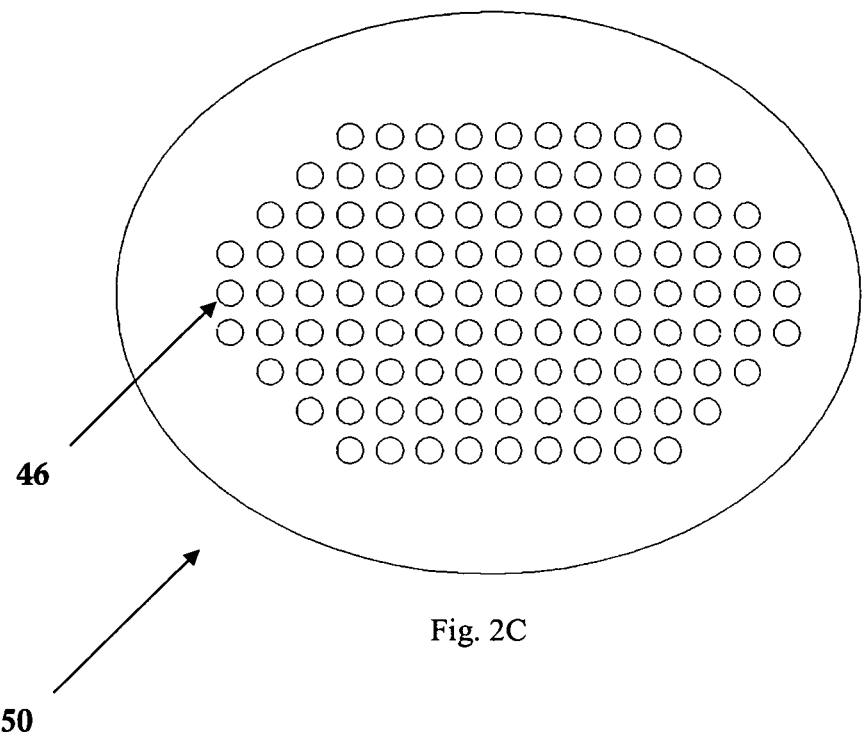
FIG. 2C is a plan view of a film used to make tissue scaffolds with 1000 micron round cell opening patterns.
Figure 2D:
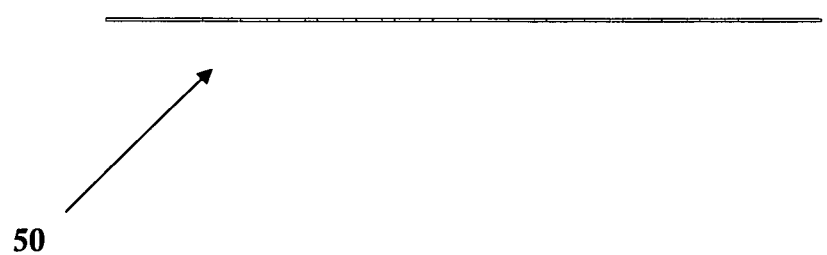
FIG. 2D is a side view of the film of FIG. 2C used to make tissue scaffolds with 1000 micron round cell opening patterns.
Figure 2E:
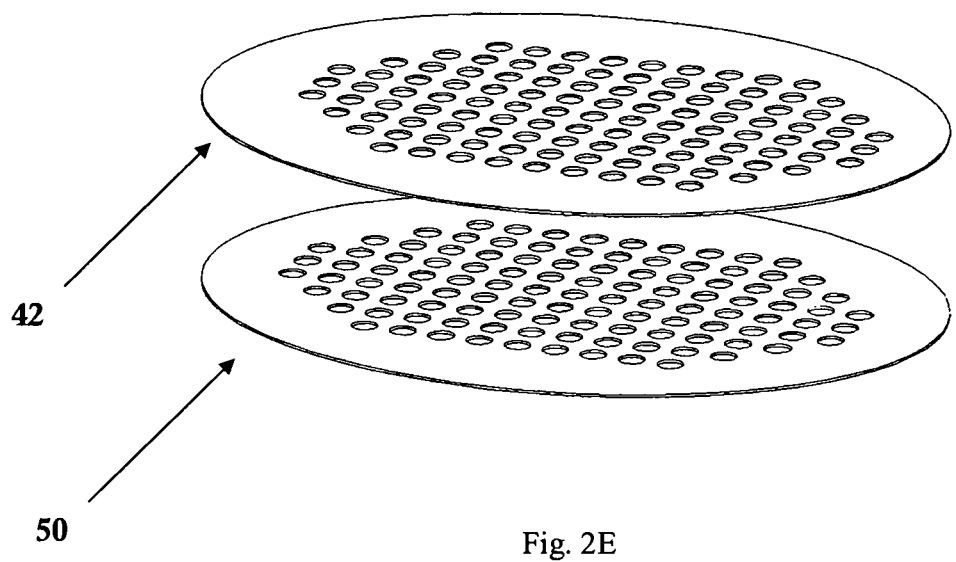
FIG. 2E is a perspective view of two films used to make tissue scaffolds with offset cell opening patterns.
Figure 2F:
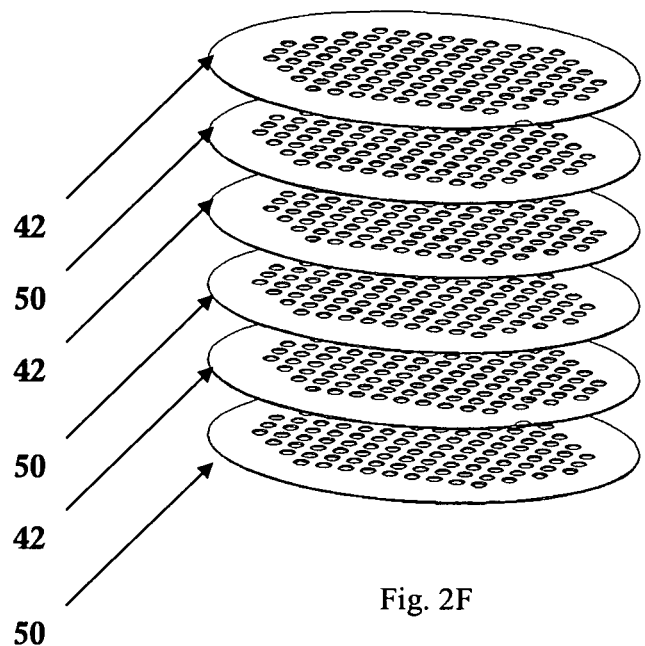
FIG. 2F is a perspective view of six films used to make tissue scaffolds with offset cell opening patterns.
Figure 2G:
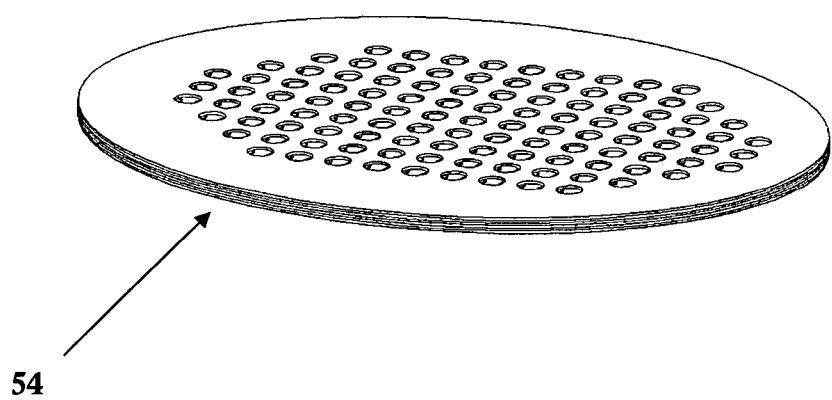
FIG. 2G is a perspective view of six films used to make tissue scaffolds with 1000 micron cell opening patterns offset by 750 microns and combined to create a 250 micron interconnecting pore.
Figure 2H:
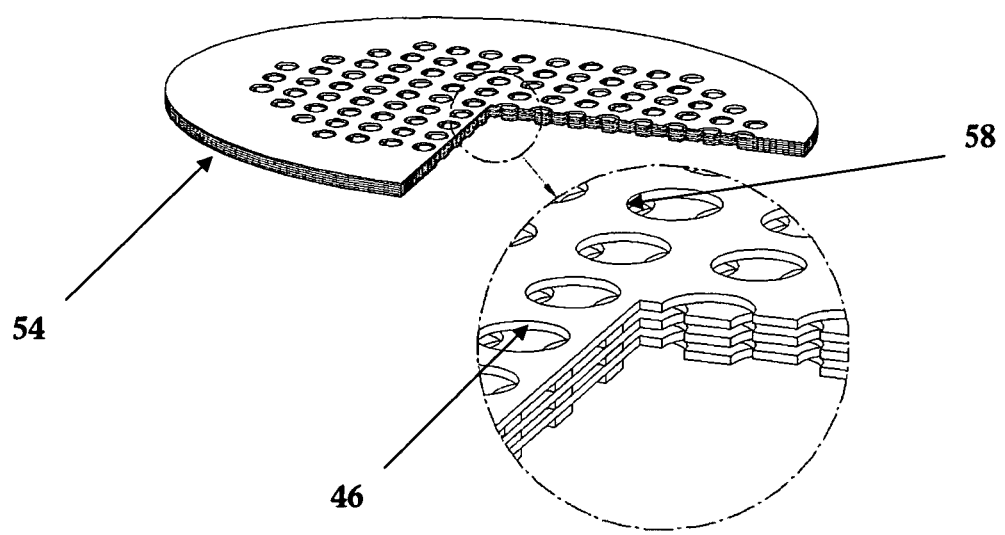
FIG. 2H is a perspective view of the six films of FIG. 2F used to make tissue scaffolds with 1000 micron cell opening patterns offset by 750 microns and combined to create a 250 micron interconnecting pores in partial section.

Referring now collectively to FIGS. 2A-2H, film layers of other embodiments including cell openings of predetermined size and configuration according to other embodiments can be combined to form a tissue scaffold. FIG. 2A illustrates a film layer 42 used to make a tissue scaffold with round 1000 micron cell openings 46 in a predetermined arrangement. The film layer 42 has known or discernable dimensions (width, length, and thickness), which can be modified or left intact during the manufacture of a tissue scaffold. Film layer 42 is a single layer. FIG. 2B is a side view of a film layer 42 used to make a tissue scaffold. FIG. 2C is a perspective view of a film layer 50 used to make a tissue scaffold with round 1000 micron cell openings 46 in a predetermined arrangement. It should be noted that the round cell openings 46 have the same dimensions for film layer 42 and film layer 50. The film layer 50 has known or discernable dimensions (width, length, and thickness), which can be modified or left intact during the manufacture of a tissue scaffold. Film layer 50 is a single layer. FIG. 2D is a side view of a film layer 50 used to make a tissue scaffold. FIG. 2E is a perspective view of film layer 42 and film layer 50 used to make a two layer tissue scaffold with different offset cell opening patterns. FIG. 2F is a perspective view of film layer 42 and film layer 50 used to make a six layer tissue scaffold with different offset cell opening patterns. FIG. 2G is a perspective view of film layers 42 and film layers 50 forming a six layer tissue scaffold 54. FIG. 2H illustrates the combination of film layers 42 and film layers 50 to create an interconnecting pore 58. The round 1000 micron cell openings 46 from the first film layer 42 are offset by 750 microns and interconnect with the round 1000 micron cell openings 46 from the second film layer 50 to create a 250 micron interconnecting pore 58.

Figure 3A:
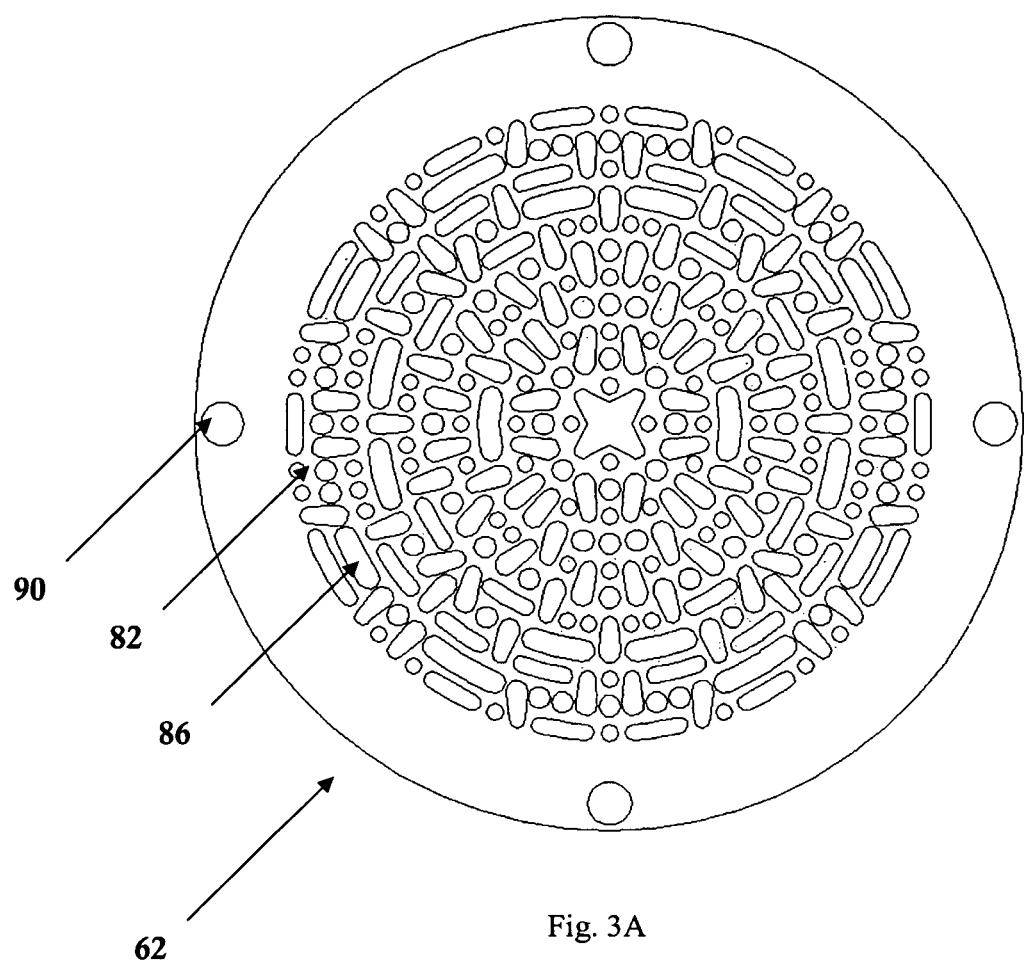
FIG. 3A is a plan view of a film used to make tissue scaffolds with 300 to 1300 micron round and oval cell opening patterns.
Figure 3B:
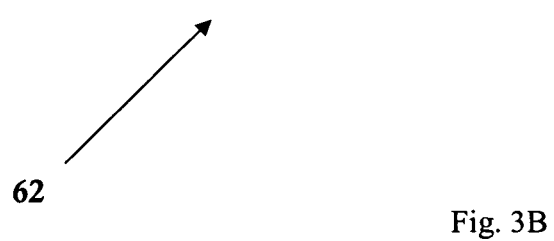
FIG. 3B is a side view of the film of FIG. 3A used to make tissue scaffolds with 300 to 1300 micron round and oval cell opening patterns.
Figure 3E:
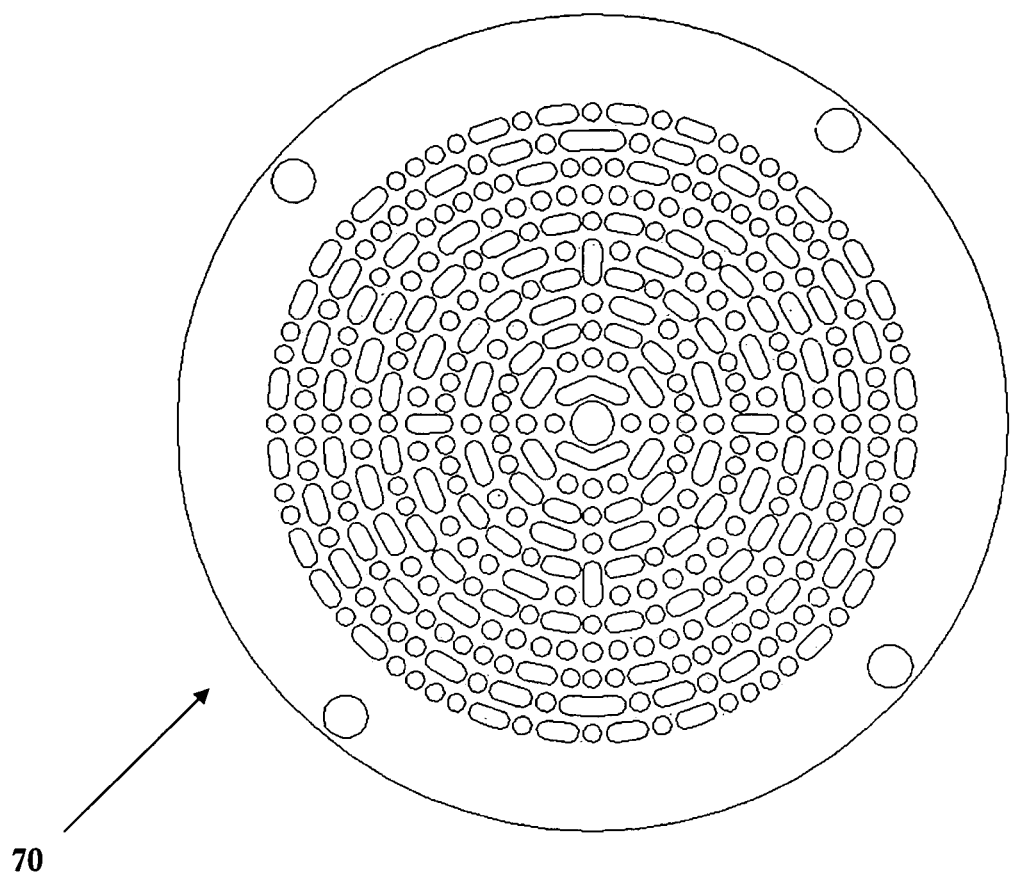
FIG. 3E is a plan view of a film used to make tissue scaffolds with 300 to 1300 micron round and oval cell opening patterns.
Figure 3F:
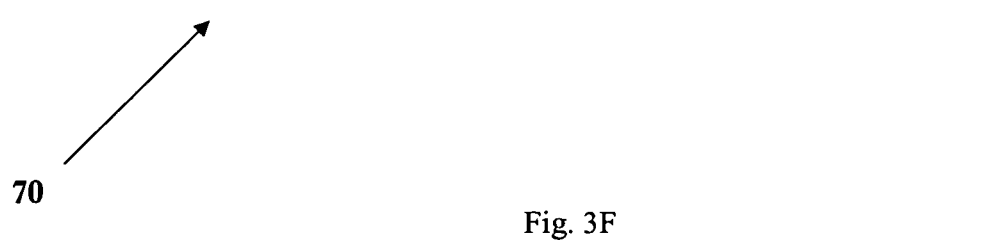
FIG. 3F is a side view of the film of FIG. 3E used to make tissue scaffolds with 300 to 1300 micron round and oval cell opening patterns.
Figure 3G:
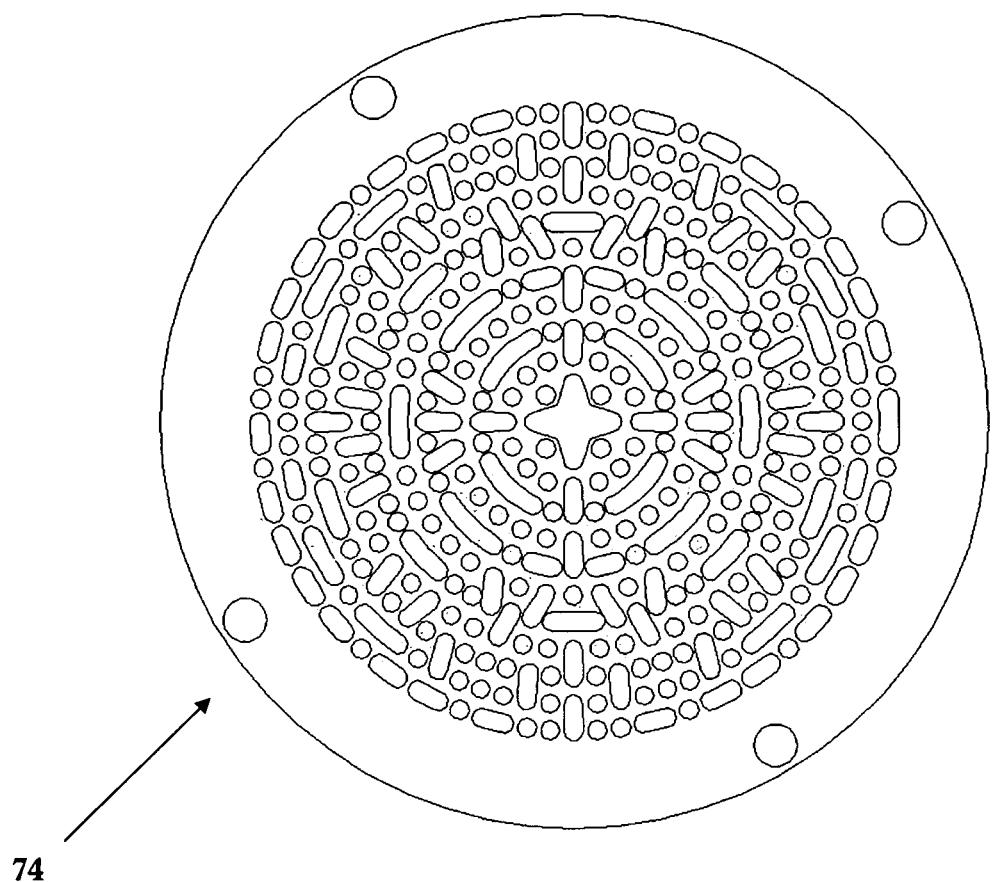
FIG. 3G is a plan view of a film used to make tissue scaffolds with 300 to 1300 micron round and oval cell opening patterns.
Figure 3H:
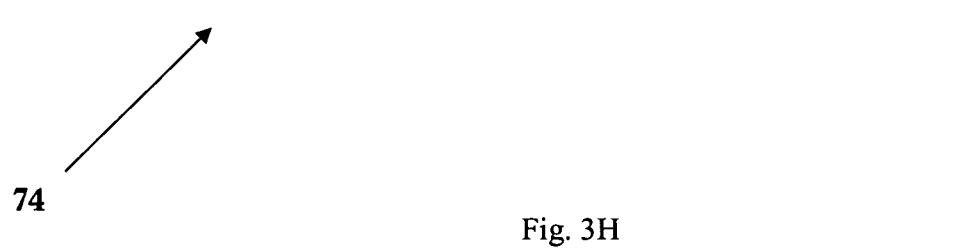
FIG. 3H is a side view of the film of FIG. 3G used to make tissue scaffolds with 300 to 1300 micron round and oval cell opening patterns.
Figure 3I:
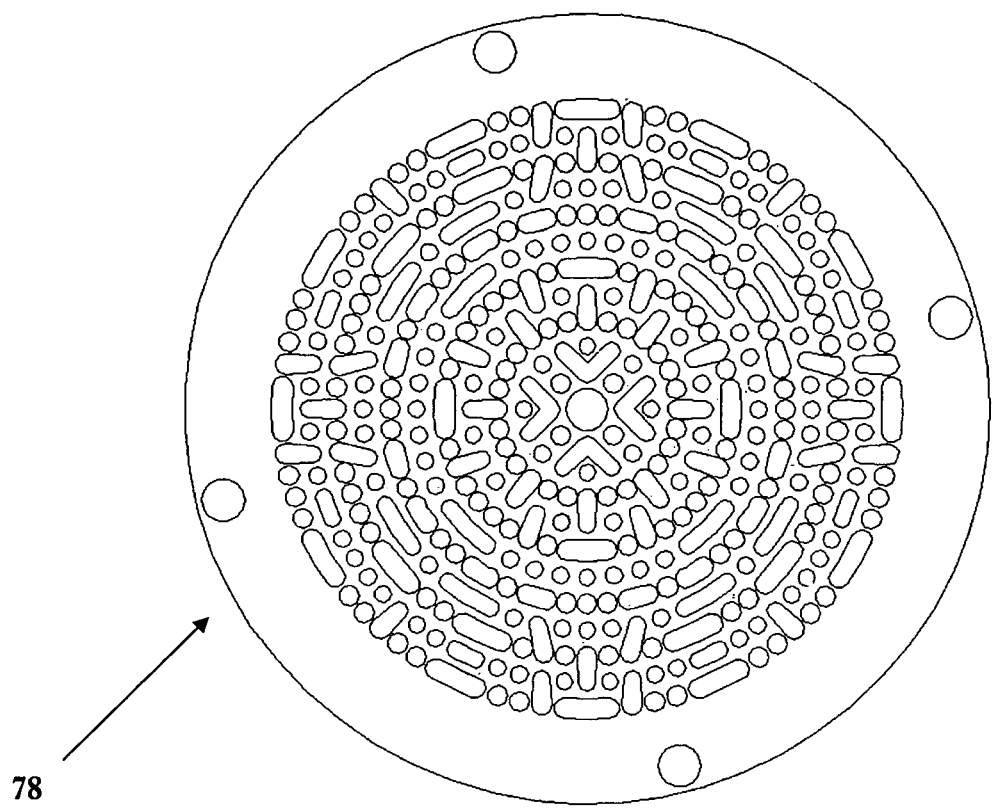
FIG. 3I is a plan view of a film used to make tissue scaffolds with 300 to 1300 micron round and oval cell opening patterns.
Figure 3J:
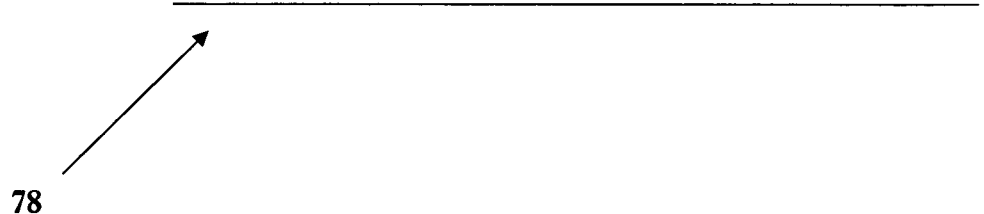
FIG. 3J is a side view of the film of FIG. 3I used to make tissue scaffolds with 300 to 1300 micron round and oval cell opening patterns.
Figure 3K:
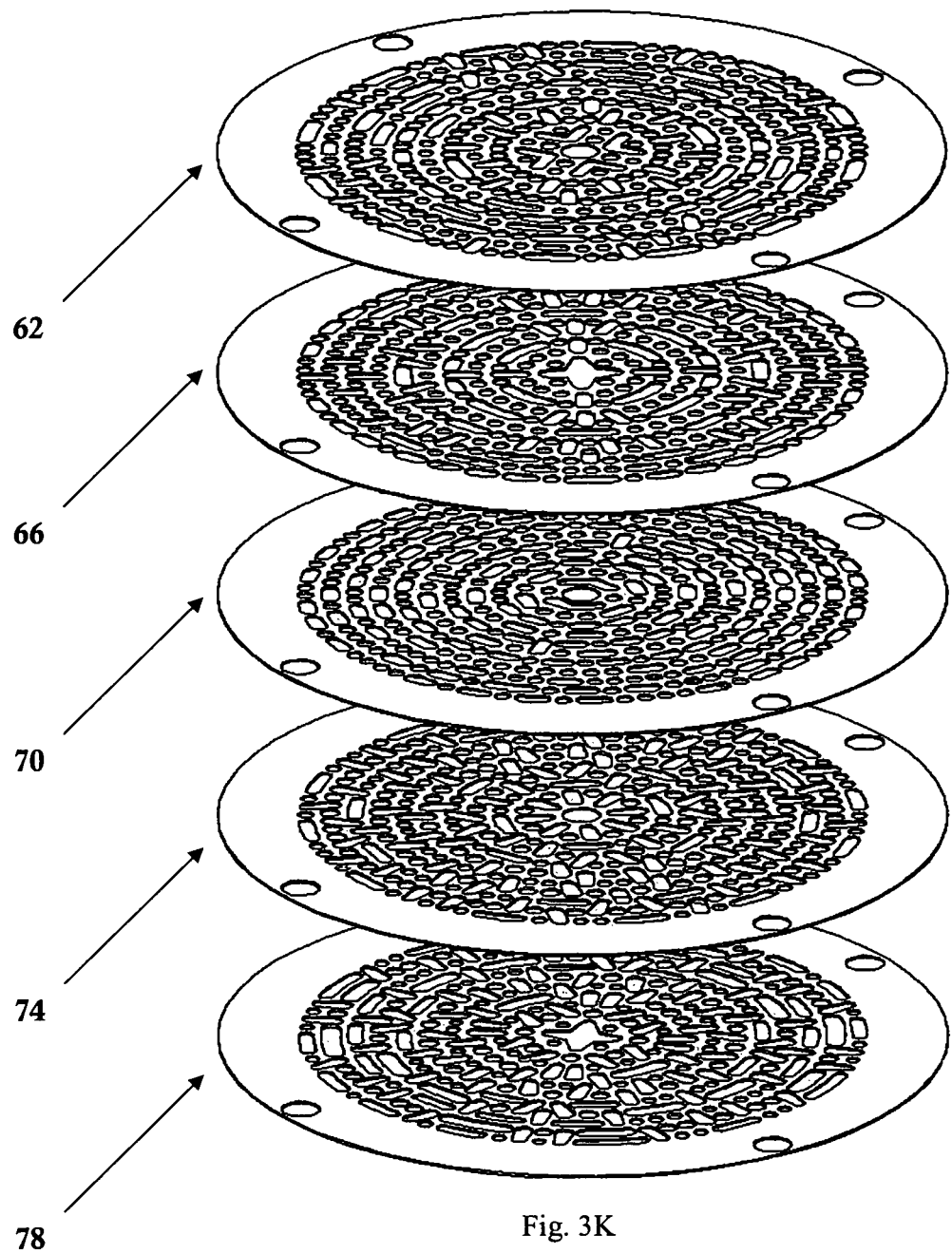
FIG. 3K is a perspective view of five films used to make tissue scaffolds with offset cell opening patterns.
Figure 3L:
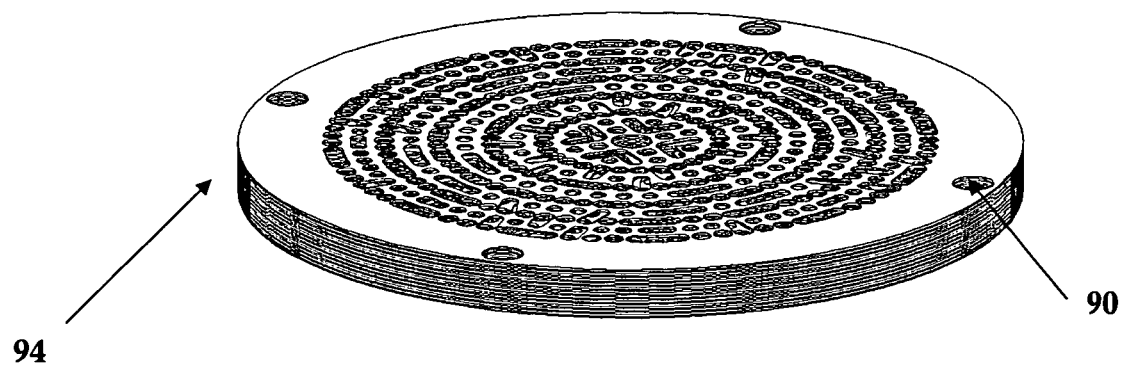
FIG. 3L is a perspective view of the five films of FIG. 3K combined to make tissue scaffolds with offset cell opening patterns.
Figure 3M:
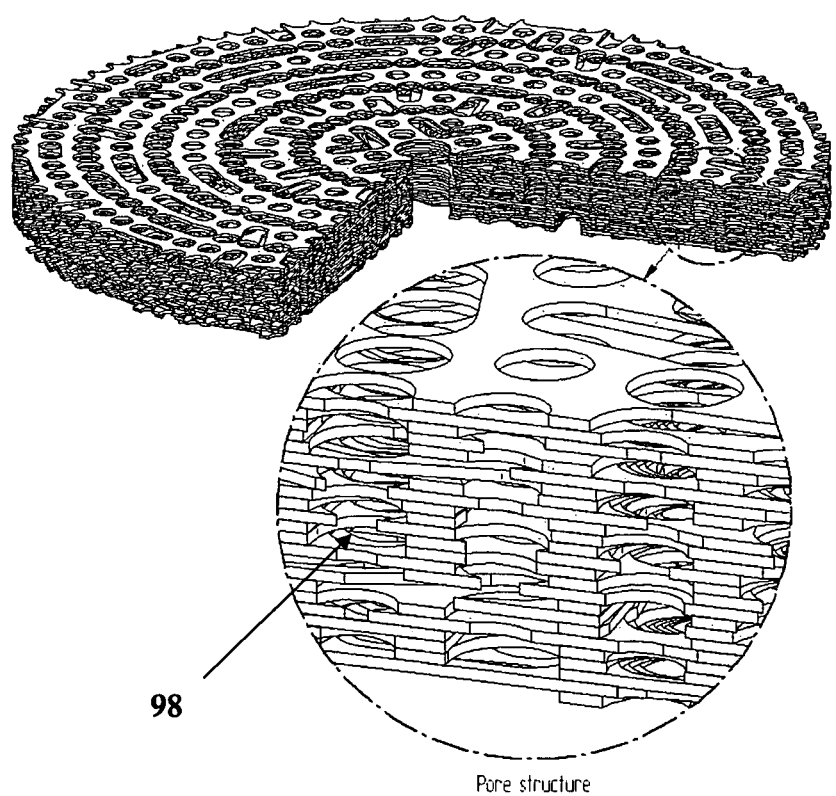
FIG. 3M is a perspective view of five films used to make tissue scaffolds with 300 to 1300 micron cell opening patterns offset and combined to create an interconnecting pores in partial section.

Referring collectively to FIGS. 3A-3M, film layers of further embodiments including cell openings of predetermined size and configuration according to other embodiments can be combined to form a tissue scaffold. FIGS. 3A-J illustrate film layers 62, 66, 70, 74, and 78 used to make a tissue scaffold with round shaped cell openings 82 and oval shaped cell openings 86 in a predetermined arrangement. The round shaped cell openings 82 and oval shaped cell openings 86 have diameters ranging from 300 microns to 1300 microns. The film layers 62, 66, 70, 74, and 78 have known or discernable dimensions (width, length, and thickness), which can be modified or left intact during the manufacture of a tissue scaffold. The film layers have alignment holes 90 to ensure the cell openings from each film layer are offset in a controlled manner. FIG. 3K is a perspective view of five film layers 62, 66, 70, 74, and 78 used to make a tissue scaffold with offset cell opening patterns. FIG. 3L is perspective view of the five film layers 62, 66, 70, 74, and 78 repeated five times to make a twenty five layer tissue scaffold 94. FIG. 3M illustrates the combination of offset film layers 62, 66, 70, 74, and 78 with cell openings to create a network of interconnecting pores 98. The outer section containing the alignment holes 90 has been removed from the tissue scaffold.

Figure 4A:
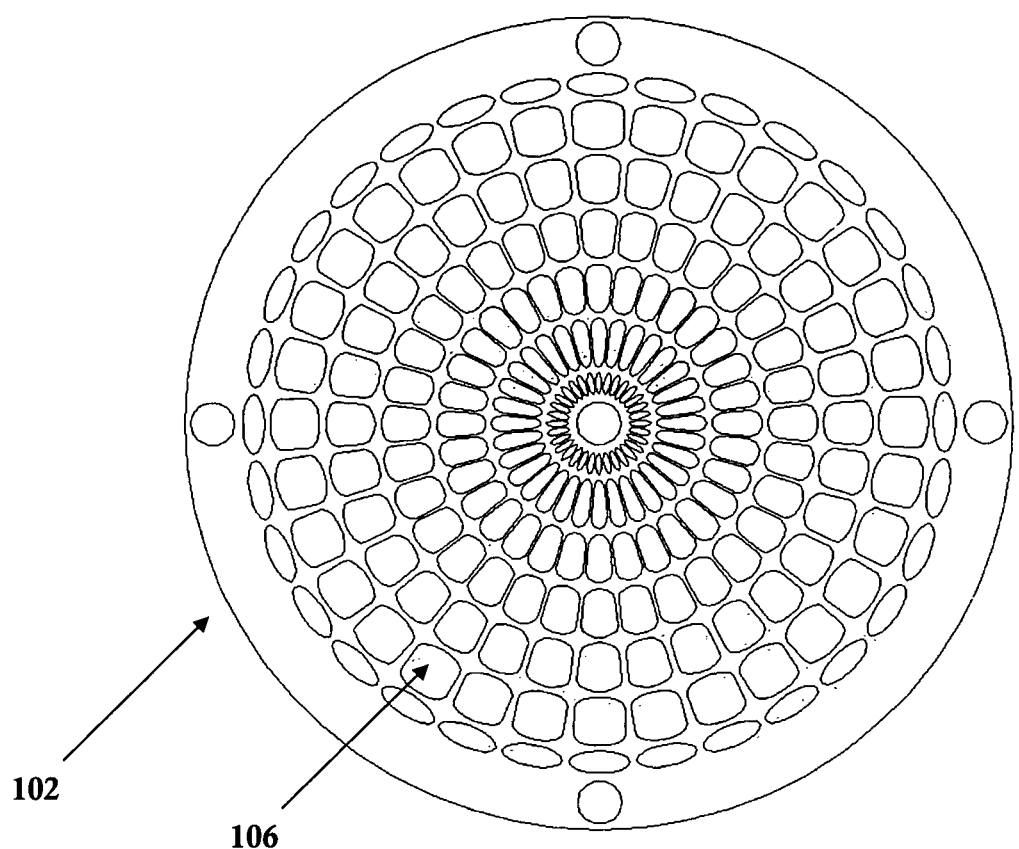
FIG. 4A is a plan view of a film used to make tissue scaffolds with 60 to 950 micron oval cell opening patterns with a gradient pattern.
Figure 4B:
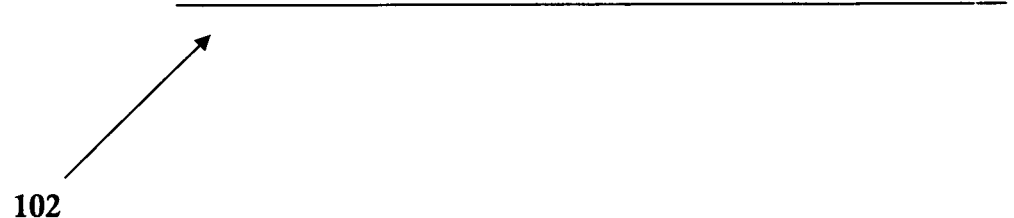
FIG. 4B is a side view of the film of FIG. 4A used to make tissue scaffolds with 60 to 950 micron round and oval cell opening patterns with a gradient pattern.
Figure 4C:
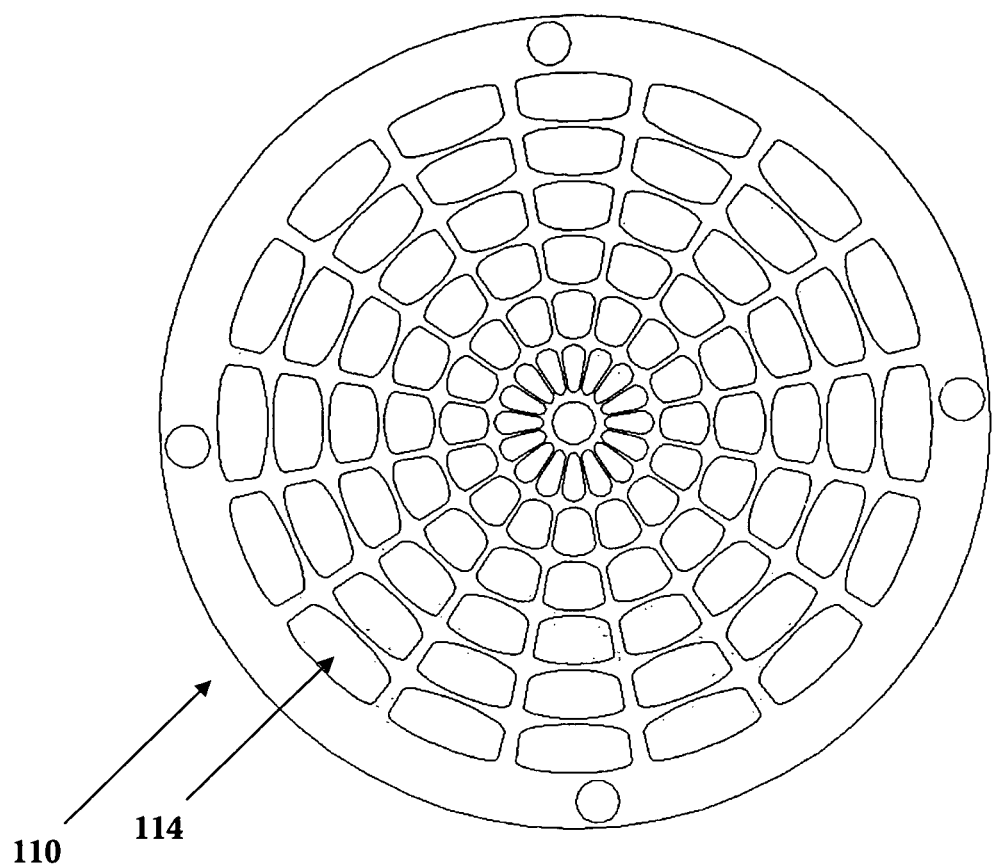
FIG. 4C is a plan view of a film used to make tissue scaffolds with 270 to 2080 micron round and oval cell opening patterns with a gradient pattern.
Figure 4D:
FIG. 4D is a side view of the film of FIG. 4C used to make tissue scaffolds with 270 to 2080 micron round and oval cell opening patterns with a gradient pattern.
Figure 4E:
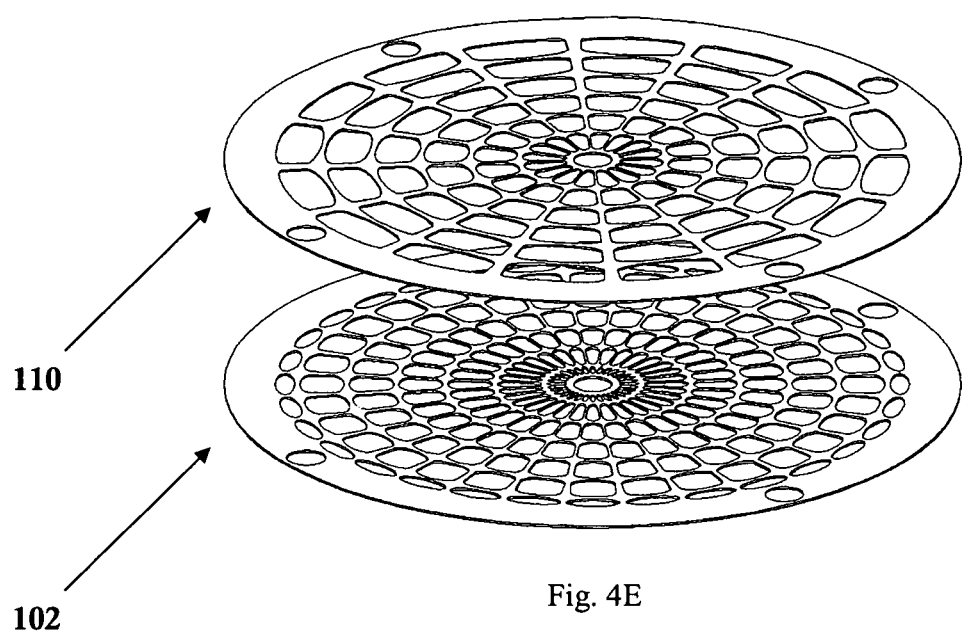
FIG. 4E is a perspective view of two films used to make tissue scaffolds with offset cell opening patterns with a gradient pattern.
Figure 4F:
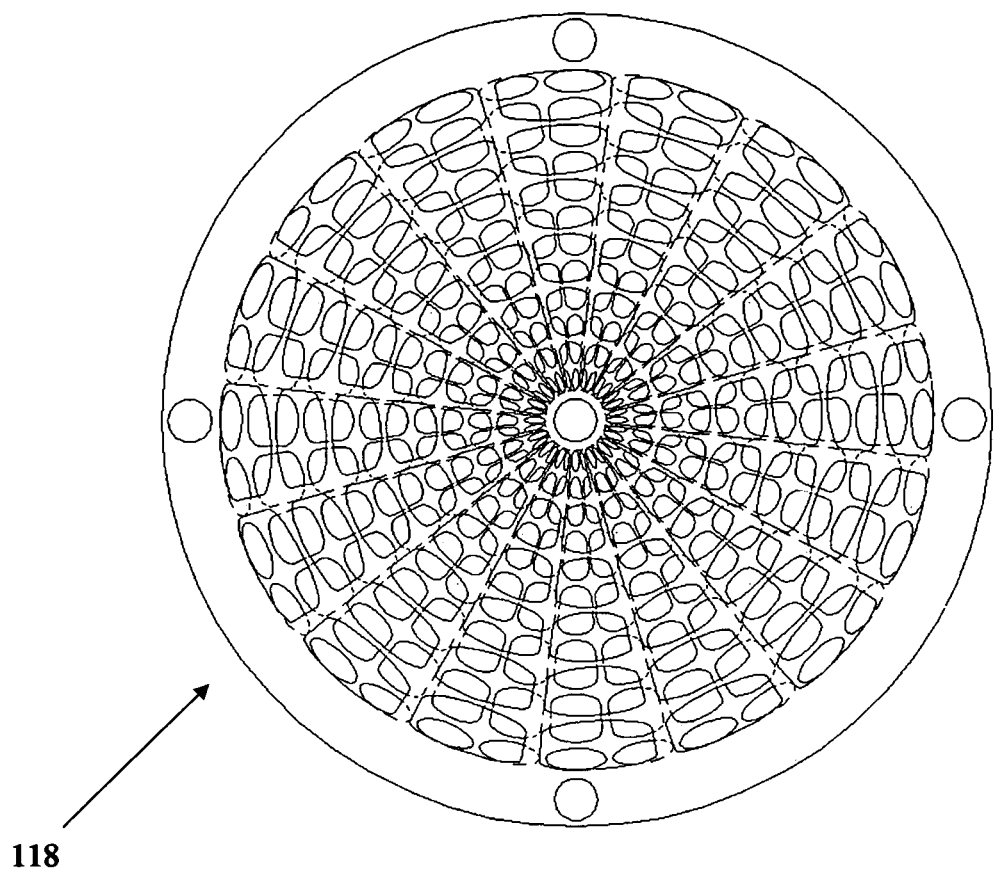
FIG. 4F is a plan view of two films combined to make tissue scaffolds with offset cell opening patterns with a gradient pattern to create an interconnecting pore scaffold with a gradient in porosity.
Figure 4G:
FIG. 4G is a side view of the two films of FIG. 4F combined to make tissue scaffolds with offset cell opening patterns with a gradient pattern to create an interconnecting pore scaffold with a gradient in porosity.
Figure 4H:
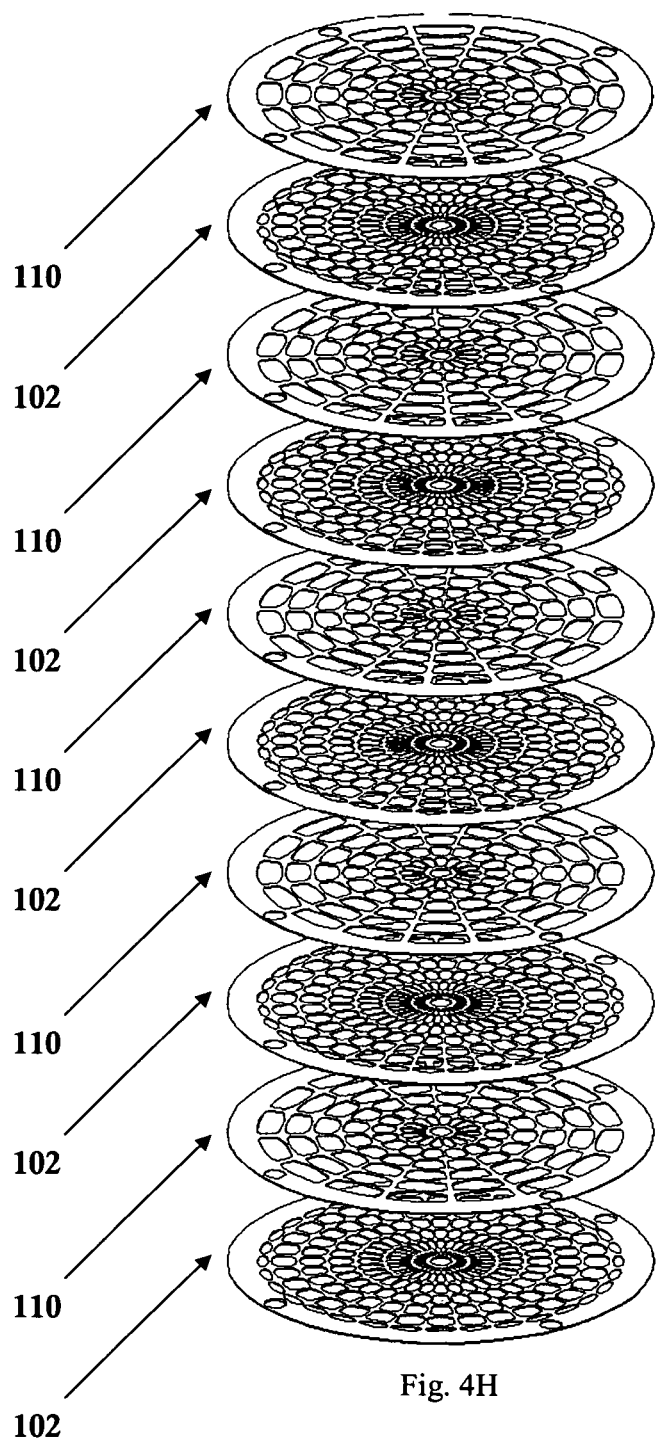
FIG. 4H is a perspective view of ten films used to make tissue scaffolds with offset cell opening patterns with a gradient pattern.
Figure 4I:
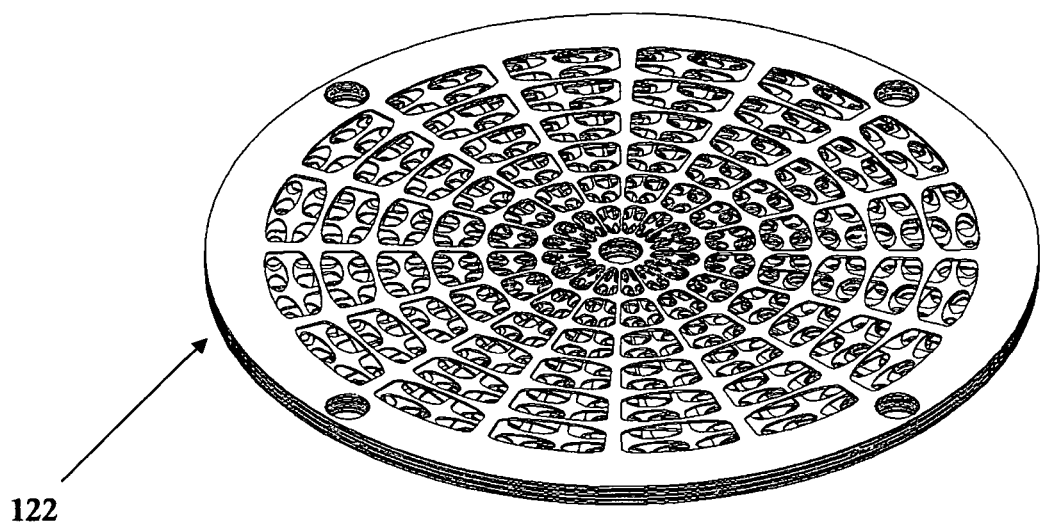
FIG. 4I is a perspective view of the ten films of FIG. 4H combined to make tissue scaffolds with offset cell opening patterns with a gradient pattern to create an interconnecting pore scaffold with a gradient in porosity.

Referring collectively to FIGS. 4A-4I, film layers of some embodiments including cell openings of predetermined size and configuration according to other embodiments can be combined to form a tissue scaffold. FIG. 4A illustrates a film layer 102 used to make a tissue scaffold with oval cell openings 106 with diameters ranging from 60 to 950 microns in a predetermined arrangement. The predetermined arrangement has a gradient of higher porosity on the edge to lower porosity in the center. The film layer 102 has known or discernable dimensions (width, length, and thickness), which can be modified or left intact during the manufacture of a tissue scaffold. Film layer 102 is a single layer. FIG. 4B is a side view of a film layer 102 used to make a tissue scaffold. FIG. 4C illustrates a film layer 110 used to make a tissue scaffold with oval cell openings 114 with diameters ranging from 270 to 2080 microns in a predetermined arrangement. The predetermined arrangement has a gradient of higher porosity on the edge to lower porosity in the center. The film layer 110 has known or discernable dimensions (width, length, and thickness), which can be modified or left intact during the manufacture of a tissue scaffold. Film layer 110 is a single layer. FIG. 4D is a side view of a film layer 110 used to make a tissue scaffold. FIG. 4E is a perspective view of film layer 102 and film layer 110 used to make a two layer tissue scaffold with different offset cell opening patterns. FIG. 4F is a perspective view of film layer 102 and film layer 110 used to make a two layer tissue scaffold 118 with different offset cell opening patterns. FIG. 4G is a side view of film layers 102 and film layers 110 forming a two layer tissue scaffold 118. The predetermined arrangement of the cell openings creates a gradient of higher porosity on the edge to lower porosity in the center which, in turn, creates a gradient of interconnecting pores with higher interconnecting areas on the edge of the tissue scaffold 118. FIGS. 4H-I are perspective views of ten film layers used to make a ten layer tissue scaffold 122.

Figure 5A:
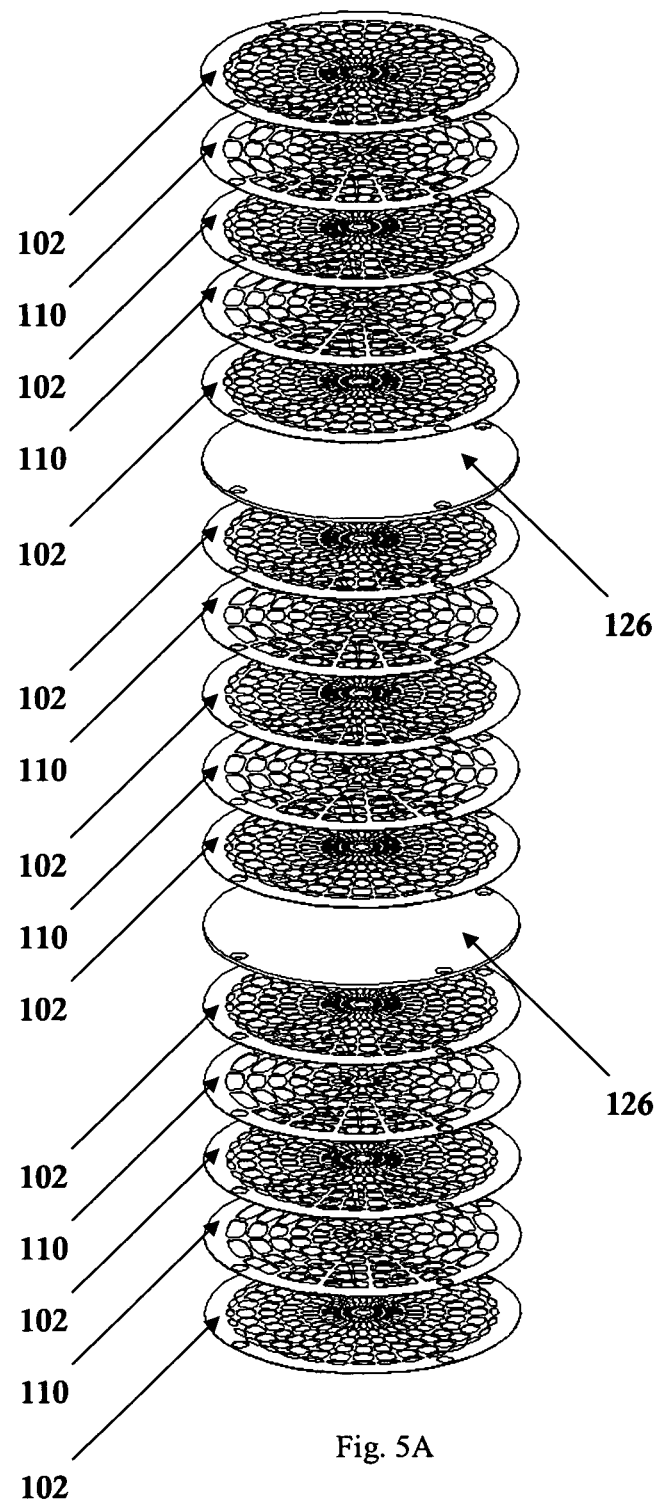
FIG. 5A is a perspective view of fifteen films used to make tissue scaffolds with offset cell opening patterns with a gradient pattern and two hydrogel films.
Figure 5B:
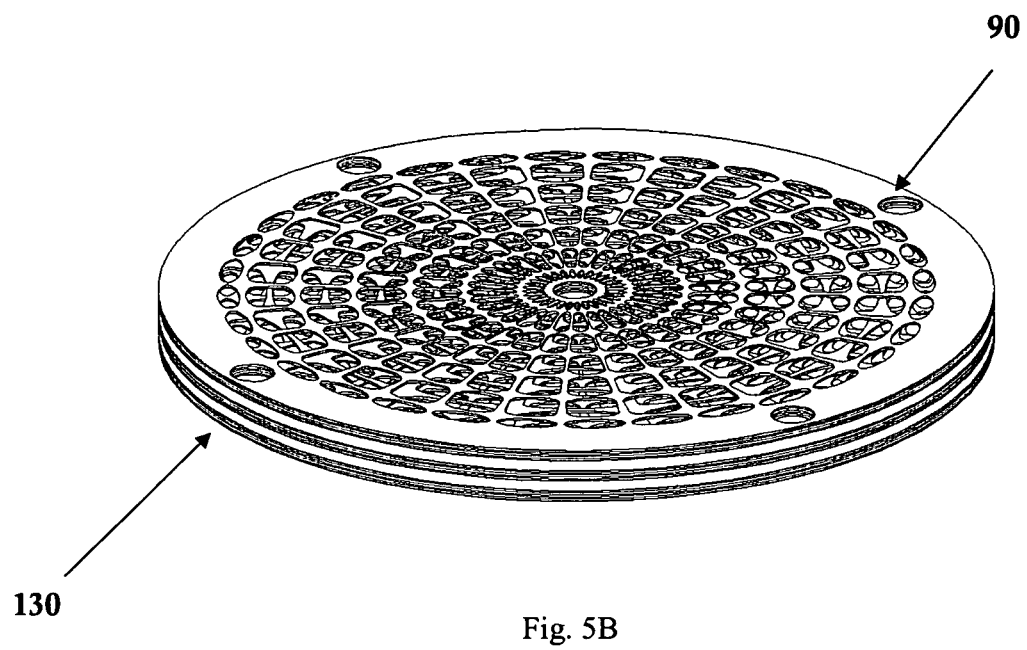
FIG. 5B is a plan view of the fifteen films of FIG. 5A combined to make tissue scaffolds with offset cell opening patterns with a gradient pattern to create an interconnecting pore scaffold with a gradient in porosity and two hydrogel films.
Figure 5C:
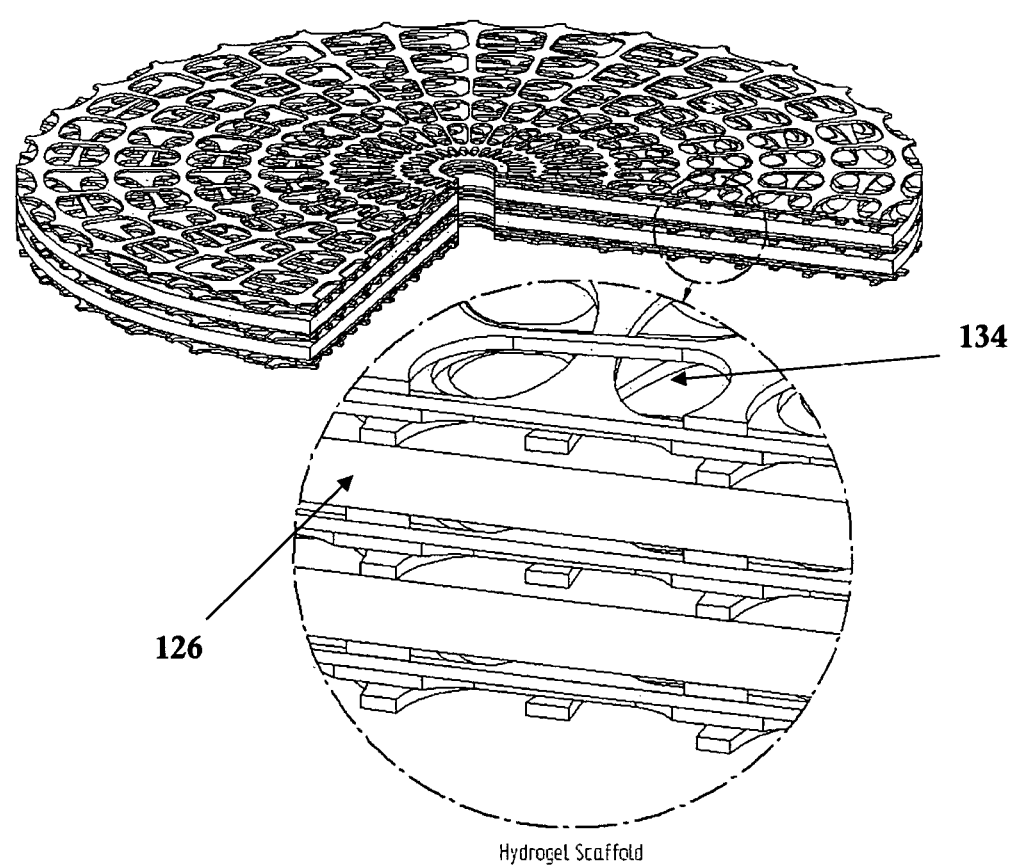
FIG. 5C is a perspective view of fifteen films combined to make tissue scaffolds with offset cell opening patterns with a gradient pattern to create an interconnecting pore scaffold with a gradient in porosity and two hydrogel films in partial section.

Referring collectively to FIGS. 5A-5C, film layers of further embodiments including cell openings and hydrogel film layers can be combined to form a tissue scaffold. FIG. 5A illustrates fifteen film layers 102 and 110 used to make a tissue scaffold with offset cell opening patterns with a gradient pattern and two hydrogel film layers 126. Film layer 102 is used with film layer 110 to make a tissue scaffold assembly. Hydrogel film layer 126 is place under film layer 102 during assembly of the tissue scaffold. The hydrogel film layer can promote cellular interaction with the tissue scaffold with or without the use of therapeutic agents. FIGS. 5B-C are perspective views of fifteen film layers used to make a tissue scaffold 130 with offset cell opening patterns forming interconnecting pores 134 with a gradient pattern and two hydrogel film layers 126. The outer section containing the alignment holes 90 has been removed from the tissue scaffold.

Figure 6A:
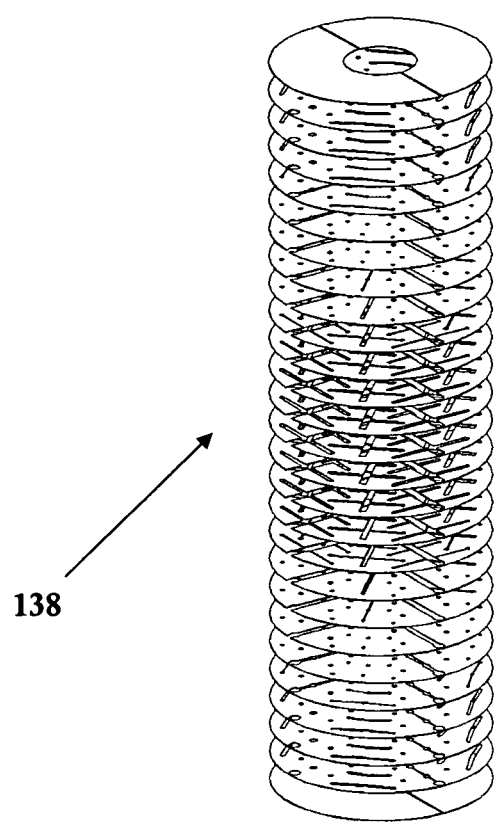
FIG. 6A is a perspective view of twenty seven films used to make a tissue scaffold with delivery channel openings within the scaffold.
Figure 6B:
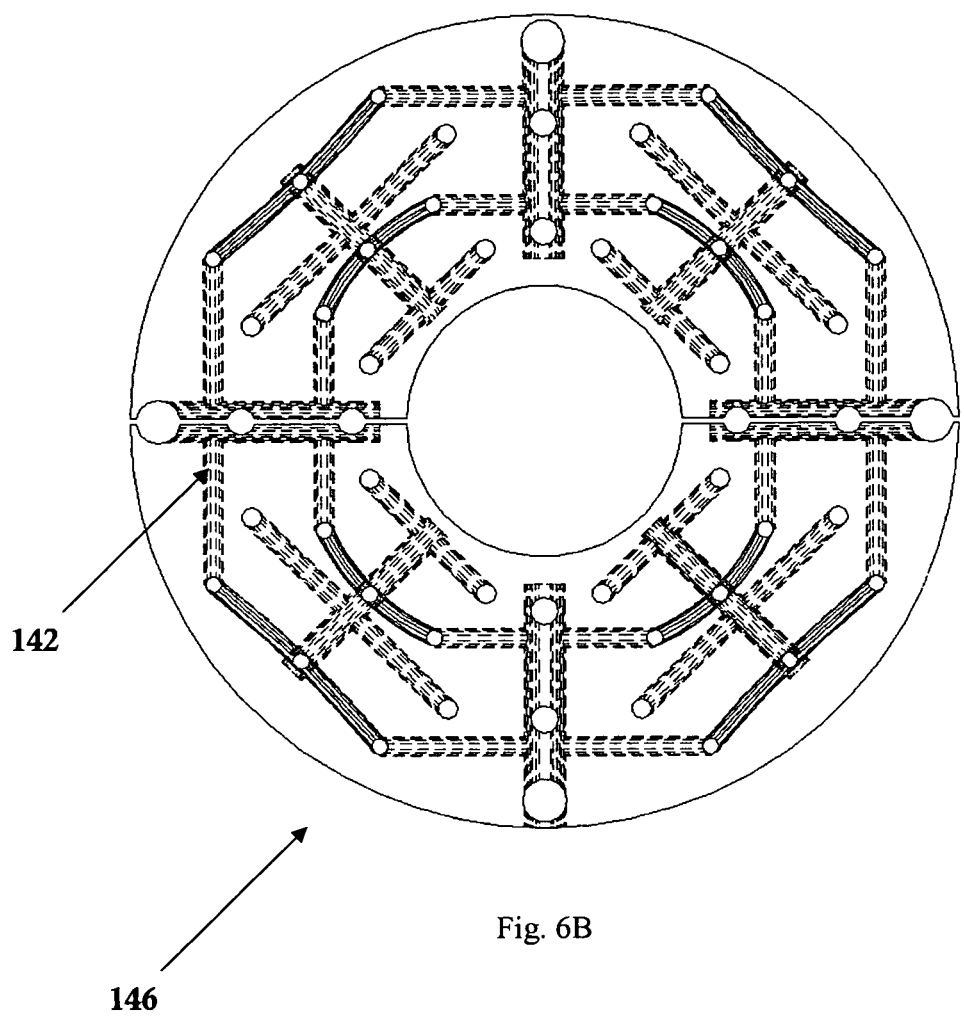
FIG. 6B is a plan view of the twenty five films of FIG. 6A combined to make a tissue scaffold with delivery channel openings within the scaffold.
Figure 6C:
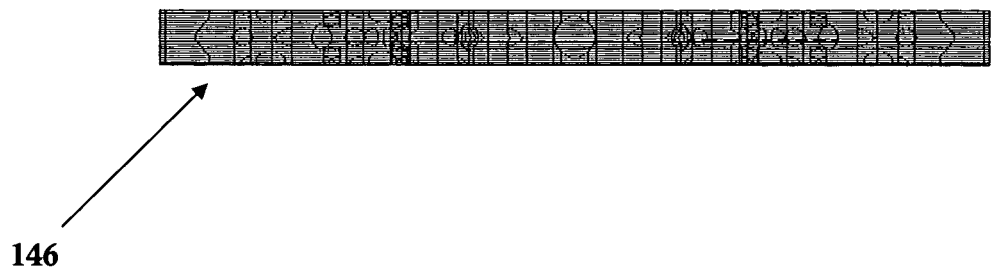
FIG. 6C is a side view of the twenty five films of FIG. 6A combined to make a tissue scaffold with delivery channel openings within the scaffold.
Figure 6D:
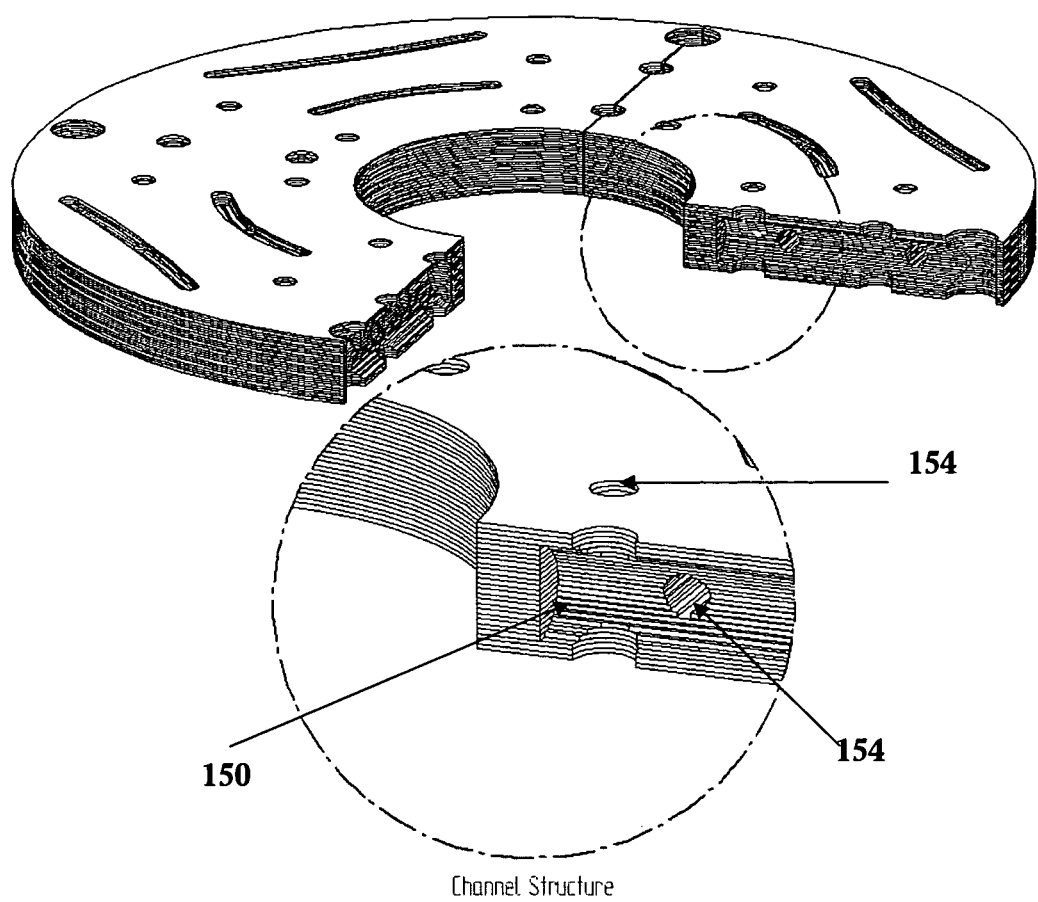
FIG. 6D is a perspective view of the twenty five films of FIG. 6A combined to make a tissue scaffold with delivery channel openings within the scaffold in partial section.
Figure 6E:
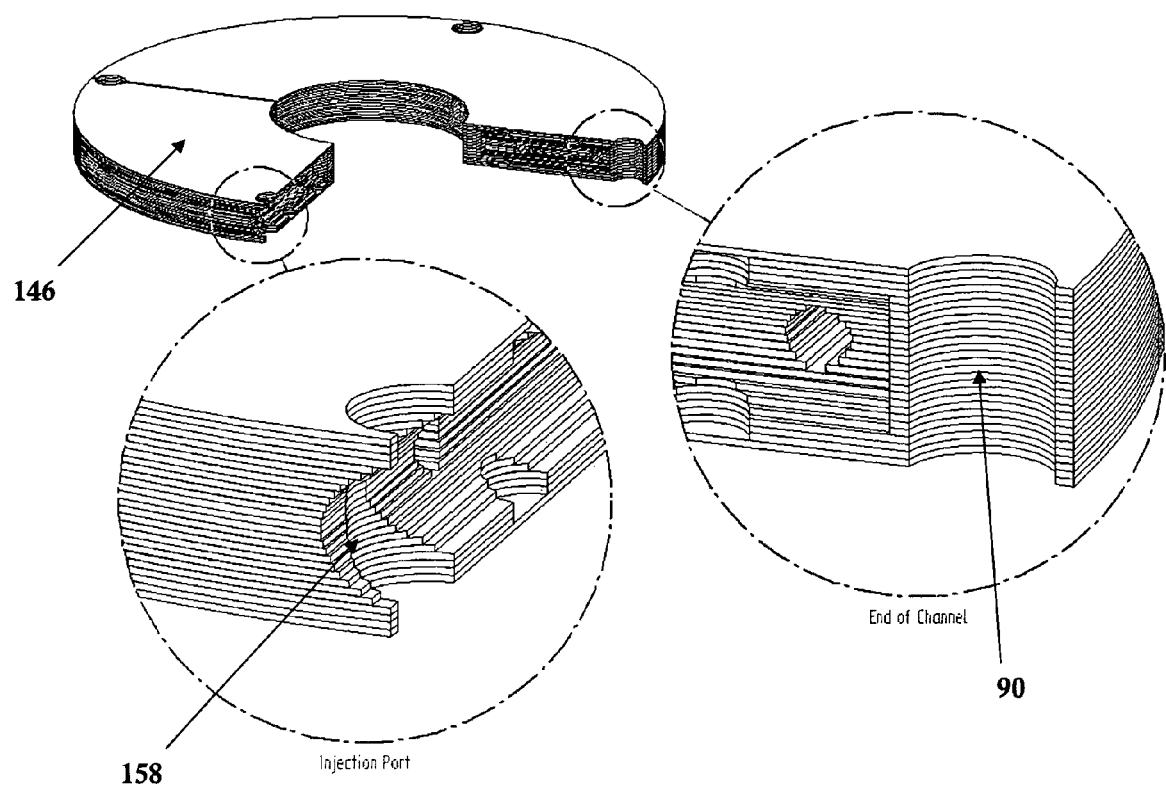
FIG. 6E is a perspective view of twenty seven films combined to make a tissue scaffold with delivery channel openings within the scaffold with a cut out section and isolated on the top and bottom in partial section.
Figure 6F:
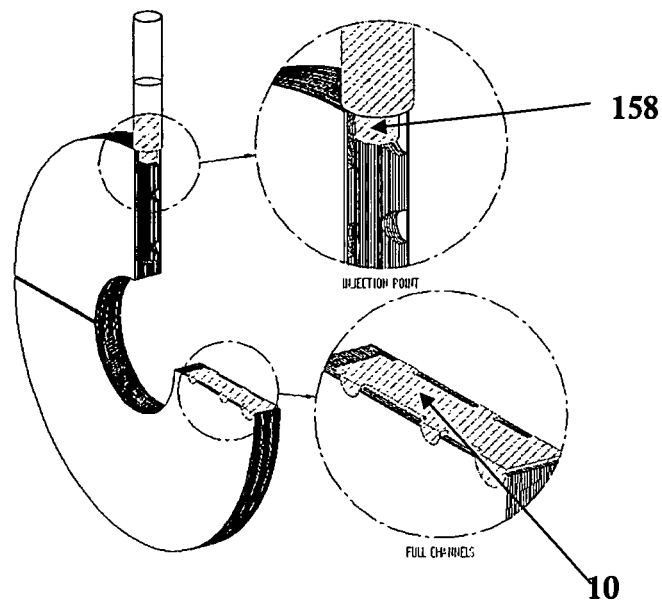
FIG. 6F is a perspective view of twenty seven films combined to make a tissue scaffold with delivery channel openings within the scaffold in partial section to depict the process of delivering agents or cells to the channel openings.
Figure 6G:
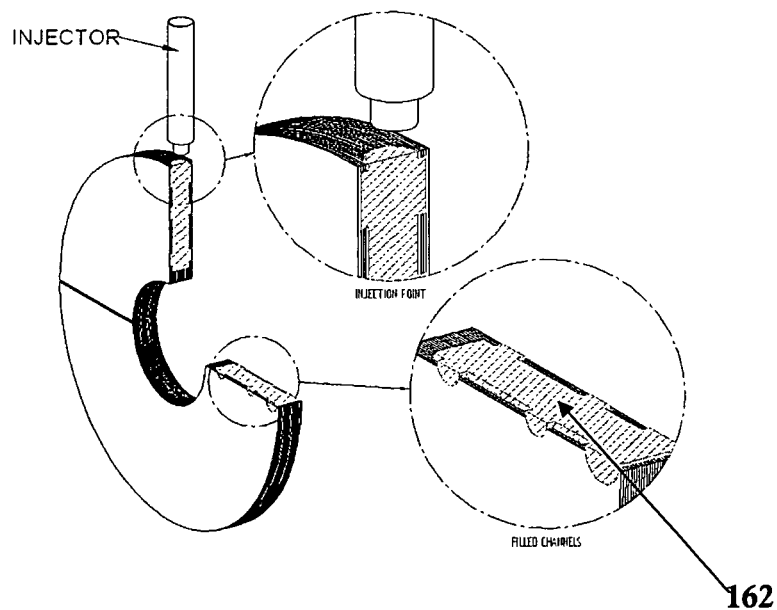
FIG. 6G is a perspective view of twenty seven films combined to make a tissue scaffold with delivery channel openings within the scaffold in partial section to depict the process of delivering agents or cells to the channel openings.
Figure 6I:
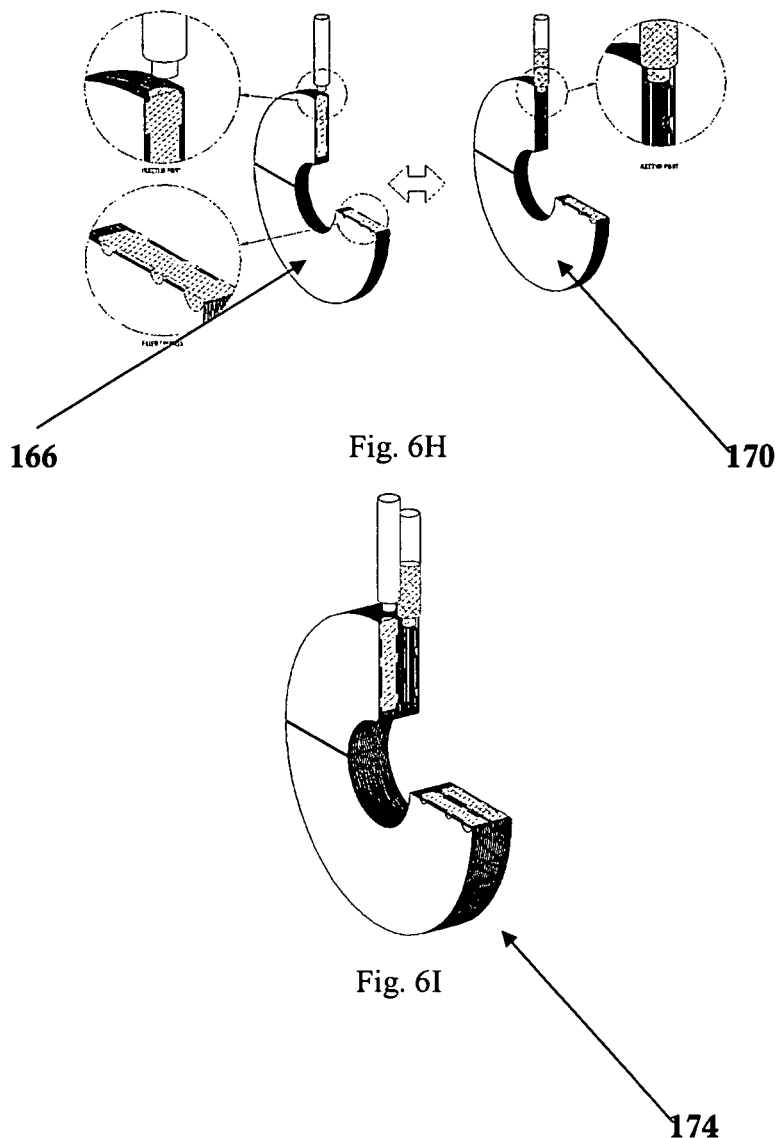
FIG. 6I is a perspective view of two separate tissue scaffolds combined to make a composite tissue scaffold with separate delivery channel openings within each scaffold in partial section depicting delivering agents or cells to the channel openings.
Figure 6J:
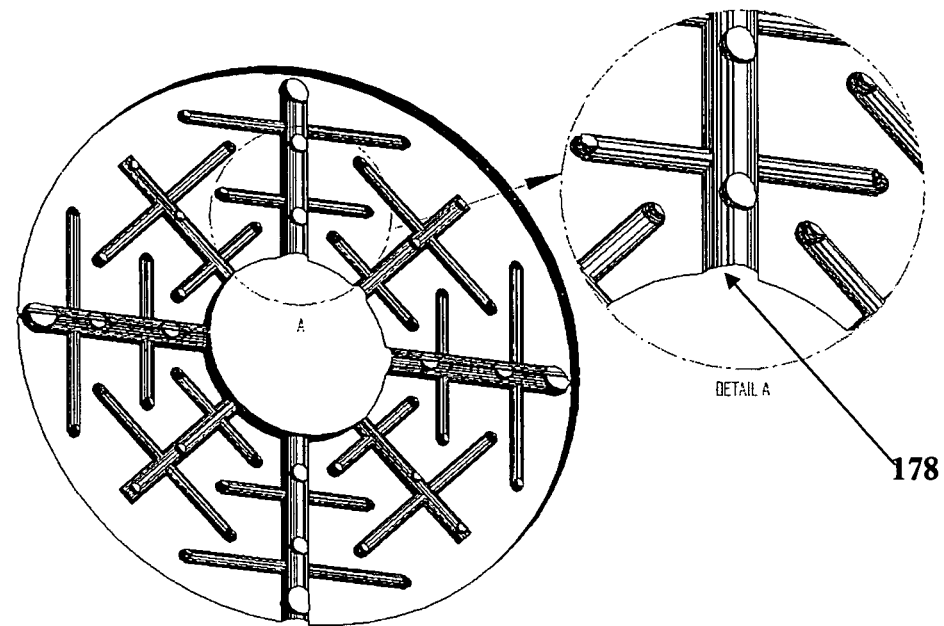
FIG. 6J is a perspective view of twenty five films combined to make a tissue scaffold with ingrowth channel openings within the scaffold that extend to the center of the scaffold.
Figure 6K:
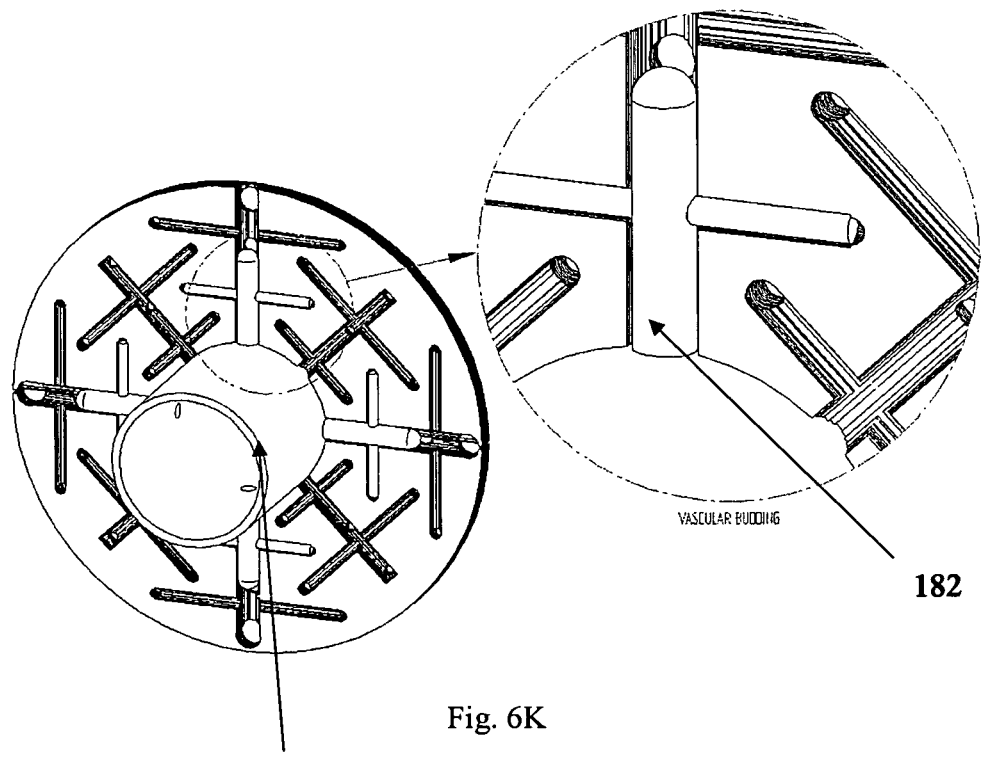
FIG. 6K is a perspective view of twenty five films combined to make a tissue scaffold with ingrowth channel openings within the scaffold that extend to the center of the scaffoldand depicting a blood vessel growing into the channels of the scaffold.

Referring collectively to FIGS. 6A-6K, film layers including delivery channel openings are combined to form a tissue scaffold. FIG. 6A illustrates twenty seven film layers 138 used to make a tissue scaffold with delivery channels 146. FIG. 6B is a perspective view of twenty five film layers 138 used to make a tissue scaffold with delivery channels. FIG. 6C is a side view of a film layers 138 used to make a tissue scaffold. FIG. 6D is a perspective view of twenty five film layers 138 combined to make a tissue scaffold with delivery channels within the scaffold with a cut out section depicting large delivery channels 150 and small delivery channels 154. FIG. 6E is a perspective view of twenty seven film layers combined to make a tissue scaffold 146 with delivery channel openings within the tissue scaffold. Alignment holes 90 and delivery channel openings 158 for delivery agents or cells are also shown with a cut out section. FIG. 6F is a perspective view of twenty seven films combined to make a tissue scaffold with delivery channel openings 158 containing an injector within the scaffold with a cut out section depicting the process of delivering agents or cells 162 to the channel openings. FIG. 6G is a perspective view of twenty seven films combined to make a tissue scaffold with delivery channel openings within the scaffold with a cut out section depicting delivered agents or cells 162 to the channel openings. FIG. 6H is a perspective view of two separate tissue scaffolds 166 and 170 with separate delivery channel openings within each scaffold with a cut out section depicting delivered agents or cells to the channel openings. FIG. 6I is a perspective view of two separate tissue scaffolds 166 and 170 combined to make a composite tissue scaffold 174 with separate delivery channel openings within each scaffold with a cut out section depicting delivered agents or cells to the channel openings. FIG. 6J is a perspective sectioned view of the twenty five film layer tissue scaffold combined to make a tissue scaffold with ingrowth channel openings 178 within the scaffold that extend to the center of the scaffold. FIG. 6K is a perspective sectioned view of twenty five film layer tissue scaffold combined to make a tissue scaffold with ingrowth channel openings 178 within the scaffold that extend to the center of the scaffold. The tissue scaffold is depicted with a blood vessel 182 growing into the ingrowth channel openings 178 of the scaffold.

Figure 7A:
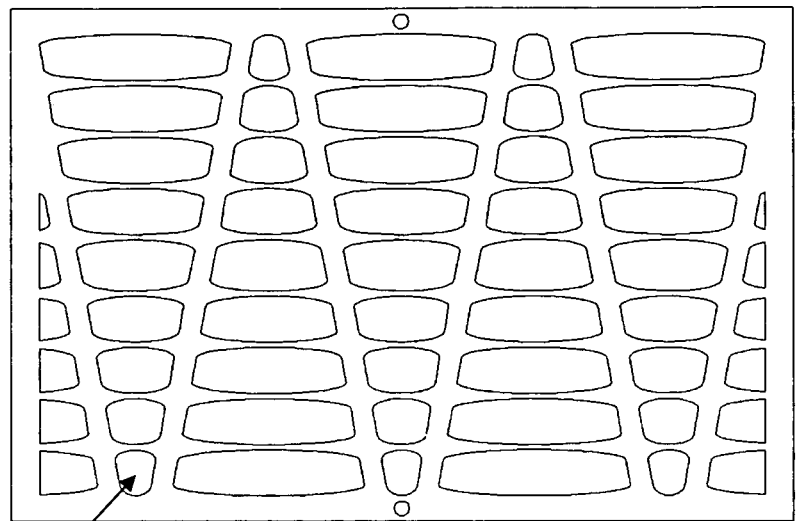
FIG. 7A is a plan view of a film used to make tissue scaffolds with oval cell opening patterns with a gradient pattern.
Figure 7B:
FIG. 7B is a side view of the film of FIG. 7A used to make tissue scaffolds with oval cell opening patterns with a gradient pattern.
Figures 7C, 7D:
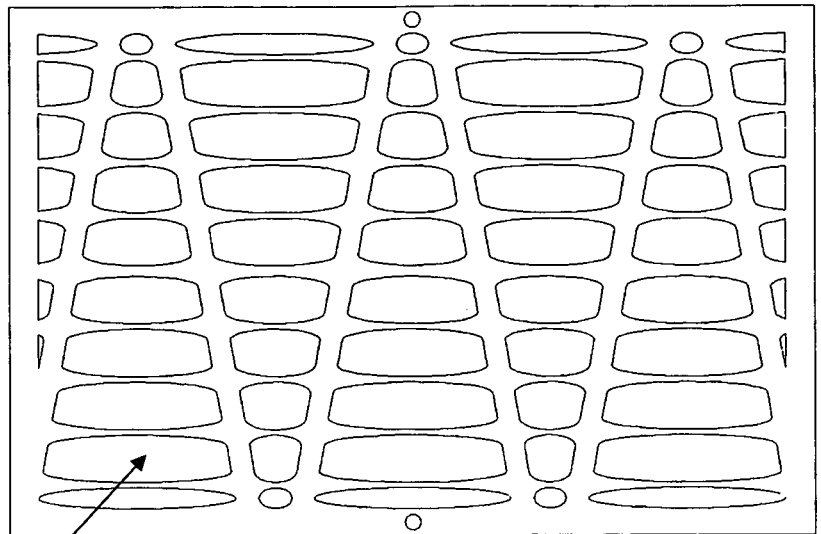
FIG. 7C is a plan view of a film used to make tissue scaffolds with oval cell opening patterns with a gradient pattern.
FIG. 7D is a side view of the film of FIG. 7C used to make tissue scaffolds with oval cell opening patterns with a gradient pattern.
Figure 7E:
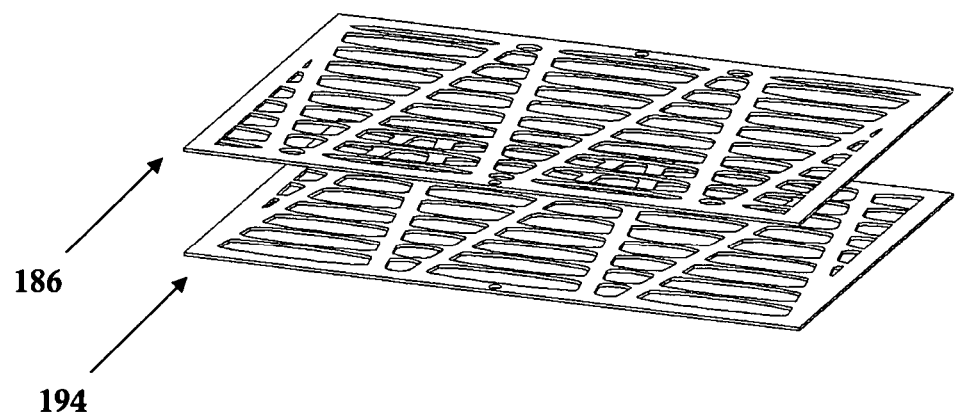
FIG. 7E is a perspective view of two films used to make tissue scaffolds with offset cell opening patterns with a gradient pattern.
Figure 7F:
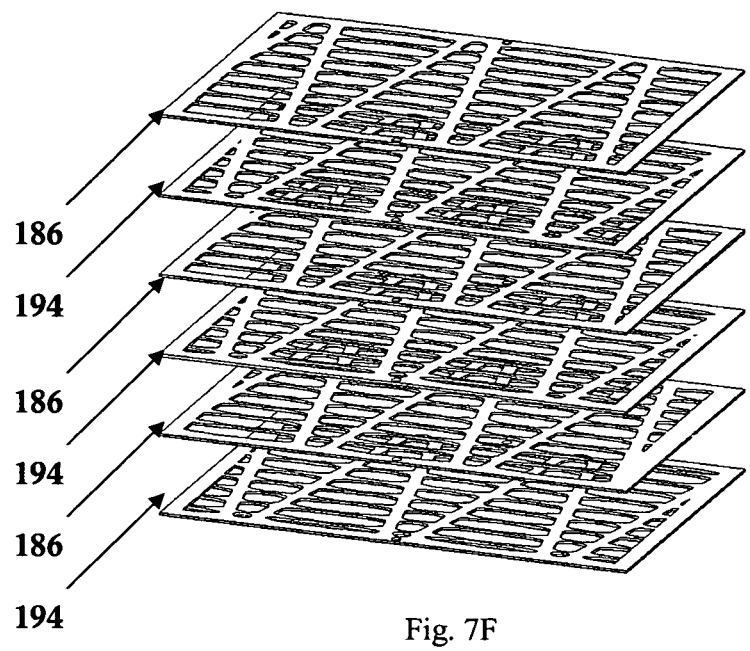
FIG. 7F is a perspective view of six films used to make tissue scaffolds with offset cell opening patterns with a gradient pattern.
Figure 7G:
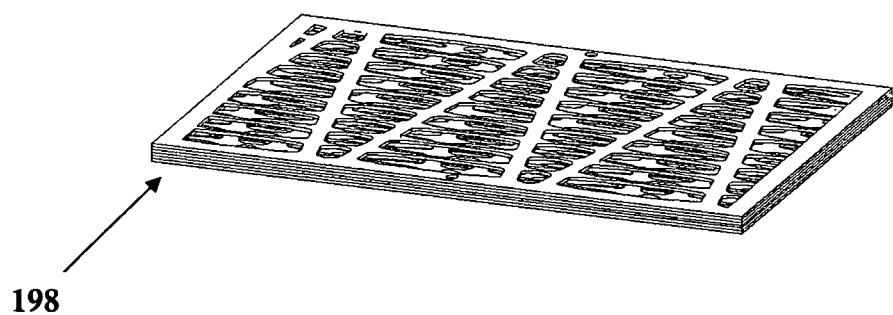
FIG. 7G is a perspective view of the six films of FIG. 7F combined to make tissue scaffolds with offset cell opening patterns with a gradient pattern to create an interconnecting pore scaffold with a gradient in porosity.
Figure 7H:
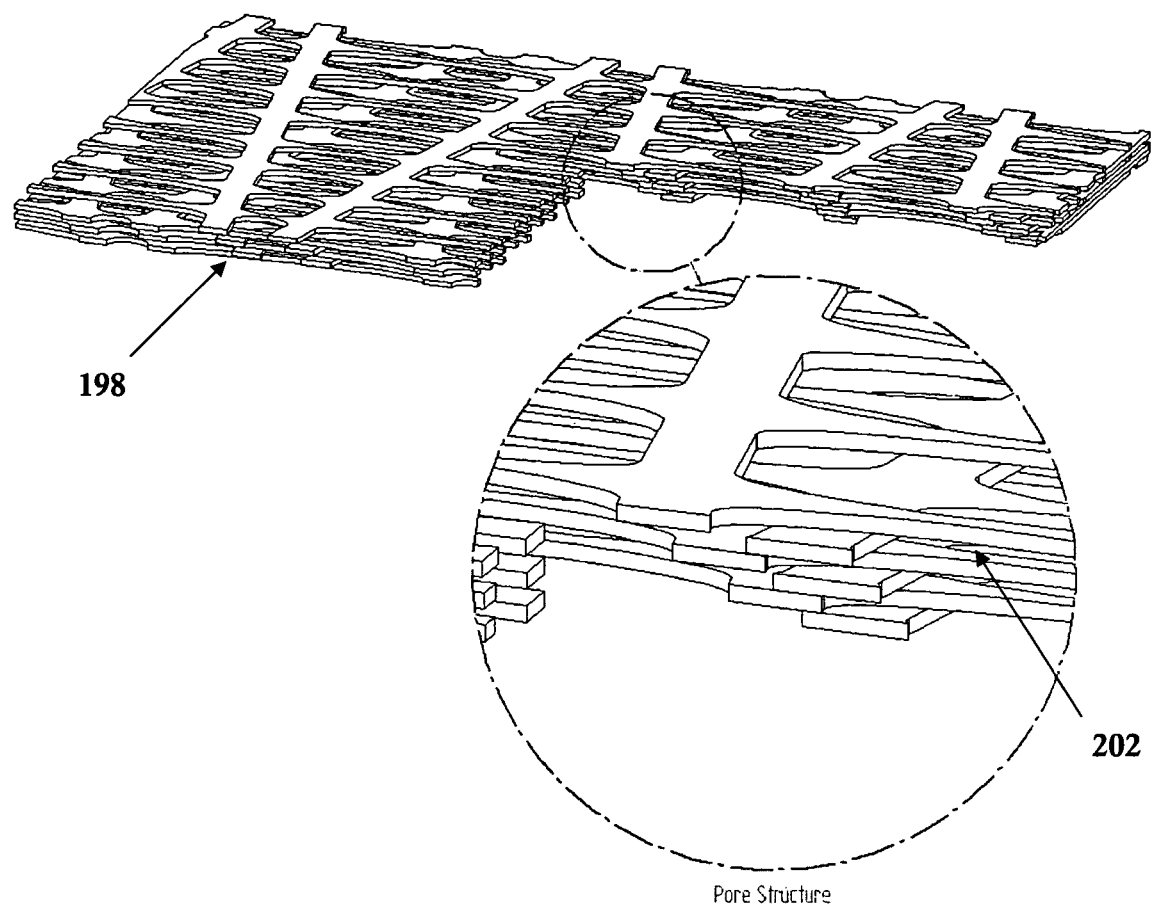
FIG. 7H is a perspective view of six films combined to make tissue scaffolds with offset cell opening patterns with a gradient pattern to create an interconnecting pore scaffold with a gradient in porosity in partial section.

Referring collectively to FIGS. 7A-7H, film layers of still further embodiments including cell openings of predetermined size and configuration are combined to form a tissue scaffold. FIG. 7A illustrates a film layer 186 used to make a tissue scaffold with oval cell openings 190 in a predetermined arrangement. The predetermined arrangement has a gradient of higher porosity in select regions to lower porosity in select regions. The film layer 186 has known or discernable dimensions (width, length, and thickness), which can be modified or left intact during the manufacture of a tissue scaffold. Film layer 186 is a single layer. FIG. 7B is a side view of a film layer 186 used to make a tissue scaffold. FIG. 7C illustrates a film layer 194 used to make a tissue scaffold with oval cell openings 190 in a predetermined arrangement. The predetermined arrangement has a gradient of higher porosity in select regions to lower porosity in select regions. The film layer 194 has known or discernable dimensions (width, length, and thickness), which can be modified or left intact during the manufacture of a tissue scaffold. Film layer 194 is a single layer. FIG. 7D is a side view of a film layer 194 used to make a tissue scaffold. FIG. 7E is a perspective view of film layer 186 and film layer 194 used to make a two layer tissue scaffold with different offset cell opening patterns. FIG. 7F is a perspective view of film layer 186 and film layer 194 used to make a six layer tissue scaffold with different offset cell opening patterns. FIGS. 7G-H are perspective views of film layers 186 and film layers 194 forming a six layer tissue scaffold 198. The predetermined arrangement of the cell openings creates a gradient of higher porosity in select regions to lower porosity in select regions which, in turn, creates a gradient of interconnecting pores 202 with higher interconnecting areas in select regions of the tissue scaffold 198.

Figure 8:
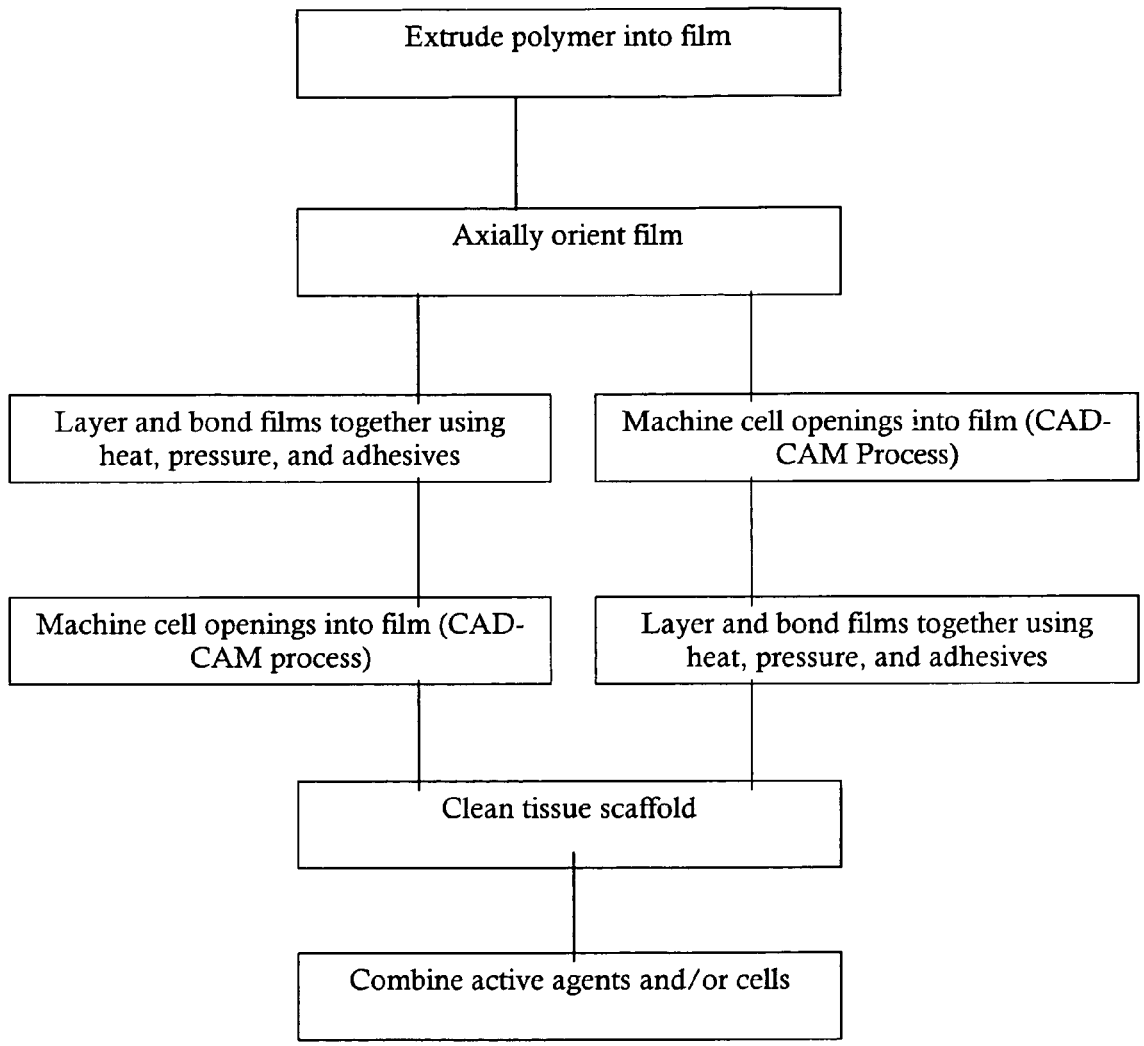
FIG. 8 is a flow chart depicting a method of producing a tissue scaffold.

FIG. 8 is a flow chart illustrating some of the steps in a method of producing a tissue scaffold of the present invention.

EXAMPLES

Example 1

A tissue scaffold was constructed using a copolymer film of polylactic acid (PLA) and polycaprolactone (PCL). A tissue scaffold measuring 6000 microns in thickness was fabricated by combining six 1000 micron thick film layers with round 1000 micron cell openings. Three of the films had the cell pattern depicted in FIG. 2A and three of the films had the cell pattern depicted in FIG. 2C. A 100 watt $CO^2$ laser was used to create the cell openings in the film layers using a CAD-CAM process. Because the cell openings in film layers were machined to the specifications outlined in FIGS. 2A and 2C, the cell openings were offset by 750 microns. Consequently, interconnecting pores measuring 250 microns were created between the cell openings in the film layers. Six film layers were built up to create the scaffold. A 4061 cyanoacrylate adhesive manufactured by Henkel Loctite (Hertfordshire, UK) was used to bond the film layers together.

Example 2

The scaffold created in Example 1 can be used as a scaffold for evaluating cellular behaviour in a three-dimensional environment. The scaffold can be included in a kit that includes a sterile polystyrene tissue culture plate with the standard number of wells 6, 12, 24, 48 or 96 within which the scaffolds have been placed, instructions for the cellular seeding and/or optimal dispersion concentration of growth/active factors, and accessory tools for proper scaffold handling. In a different approach, the invention can feature a kit that includes sterile pre-formed three-dimensional scaffold shapes, a lyophilized or a combination of lyophilized growth/active factor(s), associated tools to allow the delivery of the lyophilized agents homogenously within the scaffold, and instructions for proper growth/active factor dispersion. In a different approach, the invention can feature a kit that includes sterile pre-formed 3D scaffold shapes, a lyophilized or a combination of lyophilized growth/active factor(s), a photopolymerizable agent, a vial to mix the photopolymerizable agent with the lyophilized compound, associated tools to allow the homogenous distribution of the photopolymerizable agent plus lyophilized compound into the scaffold, and necessary instructions. The kit could or could not include a light source to induce local photopolymerization, thus, trapping of the lyophilized compound into the 3D scaffold.

A number of embodiments have been described. Other embodiments are within the scope of the following claims.

What is claimed is:

1. A tissue scaffold comprising:
a first film comprising a plurality of cell openings; and
a second film adjacent the first film and comprising a plurality of cell openings offset in a predetermined arrangement from the cell openings of the first film;
wherein the cell openings of the first film interconnect with the cell openings of the second film to define pathways with interconnecting pores of controlled area extending from the first film to the second film; and
wherein the diameter of a majority of the pores is less than the diameter of the cell openings of the first and second films that define each pore.

2. The tissue scaffold of claim 1, further comprising a plurality of delivery channels extending from the first film to the second film.

3. The tissue scaffold of claim 1, wherein at least one of the first and second films further comprises alignment holes to align the cell openings of the first and second films when joined together.

4. The tissue scaffold of claim 1, wherein at least one of the cell openings comprises a therapeutic agent and, optionally, at least one of the films is an oriented film.

5. The tissue scaffold of claim 1, wherein the first and second films are attached together using a biocompatible adhesive.

6. The tissue scaffold of claim 1, wherein the first and second films are substantially circular.

7. The tissue scaffold of claim 6, wherein at least one of the first and second films comprises progressively larger cell openings along a radial direction to define a cell opening gradient.

8. The tissue scaffold of claim 1, wherein at least one of the first and second films comprises a plurality of cell openings sized and configured to define a cell opening gradient along the film.

9. The tissue scaffold of claim 1, wherein the first film comprises a first material and the second film comprises a second material, wherein the first material has a higher absorption rate than the second material.

10. The tissue scaffold of claim 1, wherein in a first orientation of the first film with respect to the second film, the cell openings of the first film are aligned with the cell openings of the second film to define a first plurality of pathways and wherein in a second orientation of the first film with respect to the second film, the cell openings of the first film are substantially offset from the cell openings of the second film to define a second plurality of pathways.

11. The tissue scaffold of claim 1, wherein the cell openings of the first and second films are sized and configured to define multiple cell opening gradients to establish pathways for preferential cell culturing.

12. The tissue scaffold of claim 1, wherein the cell openings include a diameter between about 10 to about 10,000 microns.

13. The tissue scaffold of claim 1, wherein at least one of the first and second films comprises attachment regions configured to receive surgical fastening elements.

14. The tissue scaffold of claim 1, wherein at least one of the cell openings comprises a material to substantially suppress tissue adhesion and at least one of the cell openings comprises a material to substantially promote tissue adhesion.

15. The tissue scaffold of claim 1, wherein the cell openings of the second film are offset from the cell openings of the first film to form a combination of closed cells and open cells.

16. The tissue scaffold of claim 1, wherein the scaffold is greater than 750 microns thick.

17. The tissue scaffold of claim 1, wherein the scaffold is greater than 0.5 inches thick.

18. A tissue scaffold comprising:
a first film including a first porosity; and
a second film joined to the first film and including a second porosity greater than the first porosity; and
a plurality of delivery channels extending through the first and second films in a predetermined arrangement;
wherein the first porosity and the second porosity define a controlled porosity gradient extending from the first to the second film to selectively promote cellular regeneration along the gradient; and
wherein the diameter of a majority of the delivery channels is less than the diameter of the cell openings of the first and second films that define each channel.

19. A tissue scaffold comprising:
a first film including a plurality of cell openings; and
a second film adjacent the first film, the second film including a plurality of cell openings and alignment holes;
wherein the alignment holes align the cell openings of the first film with the cell openings of the second film such that the cell openings of the first film interconnect with the cell openings of the second film to define pathways with interconnecting pores of controlled area extending from the first film to the second film; and
wherein the diameter of a majority of the pores is less than the diameter of the cell openings of the first and second films that define each pore.

20. The tissue scaffold of claim 19, wherein at least one of the first and second films comprises a plurality of cell openings sized and configured to define a cell opening gradient along the film.

21. The tissue scaffold of claim 19, wherein in a first orientation of the first film with respect to the second film, the cell openings of the first film are aligned with the cell openings of the second film to define a first plurality of pathways and wherein a second orientation of the first film with respect to the second film, the cell openings of the first film are substantially offset from the cell openings of the second film to define a second plurality of pathways with interconnecting pores of controlled area extending from the first film to the second film.

22. The tissue scaffold of claim 19, wherein at least one of the first and second films comprises attachment regions configured to receive surgical fastening elements.

23. The tissue scaffold of claim 19, wherein the cell openings of the second film are offset from the cell openings of the first film to form a combination of closed cells and open cells.

24. The tissue scaffold of claim 19, wherein the scaffold is greater than 750 microns thick.

25. The tissue scaffold of claim 19, wherein the scaffold is greater than 0.5 inches thick.

\* \* \* \* \*